US012653492B2

(12) United States Patent
Dagdeviren et al.

(10) Patent No.: US 12,653,492 B2
(45) Date of Patent: *Jun. 16, 2026

(54) METHODS AND APPARATUS FOR IMAGING WITH CONFORMABLE ULTRASOUND PATCH

(71) Applicant: Massachusetts Institute of Technology, Cambridge, MA (US)

(72) Inventors: Canan Dagdeviren, Cambridge, MA (US); Lin Zhang, Winchester, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/922,916

(22) Filed: Oct. 22, 2024

(65) Prior Publication Data

US 2025/0049414 A1     Feb. 13, 2025

Related U.S. Application Data

(60) Division of application No. 18/458,406, filed on Aug. 30, 2023, now Pat. No. 12,178,636, which is a
(Continued)

(51) Int. Cl.
*A61B 8/08* (2006.01)
*A61B 8/00* (2006.01)

(52) U.S. Cl.
CPC .......... *A61B 8/0825* (2013.01); *A61B 8/4209* (2013.01); *A61B 8/4477* (2013.01);
(Continued)

(58) Field of Classification Search
None
See application file for complete search history.

(56) References Cited

U.S. PATENT DOCUMENTS 3,218,825 A     11/1965  McClure
5,656,016 A      8/1997  Ogden
(Continued)

FOREIGN PATENT DOCUMENTS

WO     WO 2012/077111     6/2012
WO     WO 2015/106282     7/2015

OTHER PUBLICATIONS

U.S. Appl. No. 17/032,699, filed Sep. 25, 2020, Canan Dagdeviren, et al.

(Continued)

*Primary Examiner* — Katherine L Fernandez
(74) *Attorney, Agent, or Firm* — Daly, Crowley, Mofford & Durkee, LLP

(57)     ABSTRACT

An ultrasound patch may conform to a curved surface of a large, curvilinear part of a human body, and may capture ultrasound images of underlying tissue for detection of disease. The patch may comprise a flexible, elastomeric substrate, in which phased arrays of piezoelectric ultrasound transducers are embedded. The phased arrays may steer ultrasound beams through a wide angle to image a large volume of tissue. Mechanical deformation of the flexible substrate as it conforms to a curvilinear body part may change the relative 3D positions of the phase arrays. However, localization may be performed to detect these 3D positions. Data captured by the phased arrays may be processed, to create an ultrasound image of the underlying tissue. A semi-flexible, intermediate layer may partially encapsulate each phased array, to distribute stress at an interface between the rigid phased array and more flexible substrate.

18 Claims, 12 Drawing Sheets

Related U.S. Application Data continuation of application No. 16/658,237, filed on Oct. 21, 2019, now Pat. No. 11,779,302.

(60) Provisional application No. 62/748,442, filed on Oct. 20, 2018.

(52) U.S. Cl.
CPC ............ *A61B 8/4488* (2013.01); *A61B 8/466* (2013.01); *A61B 8/4472* (2013.01); *A61B 8/5207* (2013.01)

(56) References Cited

U.S. PATENT DOCUMENTS

| | | | |
|---|---|---|---|
| 6,120,453 | A | 9/2000 | Sharp |
| 6,478,739 | B1 | 11/2002 | Hong |
| 7,211,060 | B1 | 5/2007 | Talish et al. |
| 8,010,188 | B2 | 8/2011 | Tateno |
| 8,218,825 | B2 | 7/2012 | Gordon et al. |
| 8,968,274 | B2 | 3/2015 | Hood et al. |
| 9,069,031 | B2 | 6/2015 | Guedes et al. |
| 9,172,351 | B2 | 10/2015 | Khine et al. |
| 9,423,311 | B2 | 8/2016 | Moslehi |
| 9,720,515 | B2 | 8/2017 | Wagner et al. |
| 10,045,843 | B2 | 8/2018 | Kim et al. |
| 10,765,851 | B2 | 9/2020 | Slayton |
| 10,783,351 | B2 | 9/2020 | Hwang et al. |
| 11,088,315 | B2 | 8/2021 | Grosh et al. |
| 11,307,665 | B2 | 4/2022 | von und zu Liechtenstein |
| 11,382,987 | B2 | 7/2022 | Callan et al. |
| 11,783,627 | B2 | 10/2023 | Dagdeviren et al. |
| 12,245,871 | B2 | 3/2025 | Li et al. |
| 2005/0020921 | A1 | 1/2005 | Glassell et al. |
| 2005/0165309 | A1 | 7/2005 | Varghese et al. |
| 2005/0245826 | A1* | 11/2005 | Gervais ................ A61B 8/4209 600/443 |
| 2013/0023767 | A1 | 1/2013 | Mammone |
| 2014/0180624 | A1 | 6/2014 | Nikonov et al. |
| 2015/0148619 | A1 | 5/2015 | Berg et al. |
| 2016/0245670 | A1* | 8/2016 | Nelson ................... A61B 5/065 |
| 2017/0311924 | A1 | 11/2017 | Sudol |
| 2020/0022670 | A1* | 1/2020 | Eibl ......................... A61B 8/56 |
| 2020/0087824 | A1 | 3/2020 | Ou et al. |
| 2021/0282748 | A1* | 9/2021 | Stehle ................. A61B 8/4494 |

OTHER PUBLICATIONS

Blaber, J., et al. "Ncorr: Open-Source 2D Digital Image Correlation Matlab Software" Experimental Mechanics, vol. 55, 2015; 18 Pages.

Bu, Nan, et al. "Measuring Muscle Movements for Human Interfaces Using a Flexible Piezoelectric Thin Film Sensor" 30th Annual International Conference of the IEEE Engineering in Medicine and Biology Society; 2008; 5 Pages.

Burt, Andrew et al. "Think Multi-Site Sensors for Continuous Body Temperature Measurement" Maximum Integrated; Jan. 2014; 9 Pages.

Chen, Min, et al. "Smart Clothing: Connecting Human with Clouds and Big Data for Sustainable Health Monitoring" Mobile Networks and Applications, vol. 21; 2016; 21 Pages.

Dagdeviren, Canan, et al. "Conformal Piezoelectric Systems for Clinical and Experimental Characterization of Soft Tissue Biomechanics" Nature Materials, vol. 14, May 2015; 6 Pages.

Esposito, Daniele, et al. "A Piezoresistive Sensor to Measure Muscle Contraction and Mechanomyography" Sensors, 4, 18(8), 2553, Aug. 2018; 13 Pages.

Hughes-Riley, Theodore et al; "A Study of Thermistor Performance Within a Textile Structure"; Sensors 2017, 17, Aug. 5, 2017; 14 Pages.

Iizuka, Makito, et al. "A New Flexible Piezoelectric Pressure Sensor Array for The Noninvasive Detection of Laryngeal Movement During Swallowing" The Journal of Physiological Sciences, vol. 68, Mar. 2018; 10 Pages.

Jones; Alexander R. "The Application of Temperature Sensors into Fabric Substrates"; Master's Thesis, Kansas State University; Jan. 2011; 90 Pages.

Kang, Sung-Won et al. "The Development of an IMU Integrated Clothes for Postural Monitoring Using Conductive Yarn and Interconnecting Technology" Sensors; vol. 17, Nov. 7, 2017; 10 Pages.

Kalantarian, Haik et al. "Monitoring Eating Habits Using a Piezoelectric Sensor-Based Necklace" Computers in Biology and Medicine, vol. 58, Mar. 2015; 10 Pages.

Li, Jing, et al. "Review—Recent Progress in Flexible and Stretchable Piezoresistive Sensors and Their Applications" Journal of the Electrochemical Society, vol. 167, No. 3, Feb. 3, 2020; 23 Pages.

Linz, Torsten et al. "Fully Integrated EKG Shirt based on Embroidered Electrical Interconnections with Conductive Yarn and Miniaturized Flexible Electronics" Proceedings of the International Workshop on Wearable and Implantable Body Sensor Networks (BSN'06); Jan. 2006; 4 Pages.

Majumder, Sumit et al. "Wearable Sensors for Remote Health Monitoring" Sensors; vol. 17, No. 130; Jan. 12, 2017; 45 Pages.

Mattana, Giorgio et al. "Woven Temperature and Humidity Sensors on Flexible Plastic Substrates for E-Textile Applications" IEEE Sensors Journal; vol. 13; No. 10; Oct. 2013; 9 Pages.

Ou, Jifei et al. "SensorKnit: Architecting Textile Sensors with Machine Knitting" 3D Printing and Additive Manufacturing; vol. 6; No. 1; Jan. 2019; 12 Pages.

Paradiso, R. et al.; "Textile Electrodes and Integrated Smart Textile for Reliable Biomonitoring"; $33^{ld}$ Annual International Conference of the IEEE Engineering in Medicine and Biology Society; Aug. 30, 2011; 4 Pages.

Pan, Bing et al. "Two-Dimensional Digital Image Correlation for In-Plane Displacement and Strain Measurement: A Review" Measurement Science and Technology, vol. 20, No. 6, Apr. 2009; 18 Pages.

Paul, Gordon Mark et al. "A Smart Textile Based Facial EMG and EOG Computer Interface" IEEE Sensors Journal; vol. 14; No. 2; Feb. 2014; 8 Pages.

Ryu, Hochung et al. "A Knitted Glove Sensing System with Compression Strain for Finger Movements" Smart Materials and Structures; vol. 27; Apr. 20, 2018; 8 Pages.

Salvador, Stan et al. "Toward Accurate Dynamic Time Warping in Linear Time and Space" Intelligent Data Analysis, vol. 11, No. 5, Oct. 2007; 21 Pages.

Sayem, Abu et al. "Review on Smart Electro-Clothing Systems (SeCSs)" Creative Commons CC; Mar. 15, 2019; 34 Pages.

Scheirer, Jocelyn, et al. "Expression Glasses: A Wearable Device for Facial Expression Recognition" CHI '99 Extended Abstracts on Human Factors in Computing Systems, May 1999; 2 Pages.

Solav, Dana, et al. "MultiDIC: An Open-Source Toolbox for Multi-View 3D Digital Image Correlation" IEEE Access, Jun. 4, 2018; 16 Pages.

Solav, Dona, et al. "Bone Pose Estimation in the Presence of Soft Tissue Artifact Using Triangular Cosserat Point Elements" Annals of Biomedical Engineering, vol. 44; No. 4, Apr. 2016; 10 Pages.

Solav, Dana, et al. "Chest Wall Kinematics Using Triangular Cosserat Point Elements in Healthy and Neuromuscular Subjects" Annals of Biomedical Engineering, vol. 45, No. 8, Aug. 2017; 11 Pages.

Su, Meng, et al. "Nanoparticle Based Curve Arrays for Multirecognition Flexible Electronics" Advanced Materials, 2016; 6 Pages.

Tao, Xuyuan et al. "Bluetooth Low Energy-Based Washable Wearable Activity Motion and Electrocardiogram Textronic Monitoring and Communicating System"; Advanced Materials Technology; Jan. 2018; 6 Pages.

Varatharajan, R., et al., "Wearable Sensor Devices for Early Detection of Alzheimer Disease Using Dynamic Time Warping Algorithm" Cluster Computing; vol. 21, 2018; 10 Pages.

Xiong, Ying et al. "Compression Garments for Medical Therapy and Sports" Polymers; vol. 10; Jun. 14, 2018; 19 Pages.

Wan, Yuan, et al. "Adaptive Cost Dynamic Time Warping Distance in Time Series Analysis for Classification" Journal of Computational and Applied Mathematics, vol. 319, Aug. 2017; 7 Pages.

(56)                    References Cited

OTHER PUBLICATIONS

Zhang, Zheng, et al., "Dynamic Time Warping under Limited Warping Path Length" Information Sciences, vol. 393, July 201; 17 Pages.

Zhou, Bo et al. "Expressure: Detect Expressions Related to Emotional and Cognitive Activities Using Forehead Textile Pressure Mechanomyography" Sensors; Jan. 28, 2020; 22 Pages.

Zysset, Christoph et al.; "Textile Integrated Sensors and Actuators for Near-Infrared Spectroscopy" Optics Express; vol. 21; No. 3; Feb. 1, 2013; 12 Pages.

Bouzari et al., "Volumetric ultrasound imaging with row-column addressed 2-D arrays using Spatial Matched Filter beamforming"; 2015 IEEE International Ultrasonics Symposium (IUS); Oct. 2015.

Brem et al., "Screening Breast Ultrasound: Past, Present and Future"; American Journal of Roentgenology, vol. 204, Issue 2; Feb. 2015.

Cummins et al., "High-Frequency Ultrasound Imaging for Breast Cancer Biopsy Guidance"; Journal of Medical Imaging, 2(4):047001; Oct. 2015.

Cummins et al., "High-Frequency Ultrasound Array designed for Ultrasound-Guided Breast Biopsy"; IEEE Transactions on Ultrasonics, Ferroelectrics, and Frequency Control, vol. 63, Issue 6, pp. 817-827; Mar. 2016.

Dagdeviren et al., Conformable amplified lead zirconate titanate sensors with enhanced piezoelectric response for cutaneous pressure monitoring; Nature Communications, vol. 5, Article 4496 (2014); Aug. 2014.

Dagdeviren et al., "Conformable piezoelectric systems for clinical and experimental characterization of soft tissue biomechanics"; Nature Materials, vol. 14, pp. 728-736 (2015); May 2015.

Ben Daya et al., "Compensated Row-Column Ultrasound Imaging System Using Multilayered Edge Guided Stochastically Fully Connected Random Fields"; Scientific Reports, vol. 7, Article 10644 (2017); Sep. 2017.

Engholm et al., "Probe development of CMUT and PZT row-column-addressed 2-D arrays"; Sensors and Actuators A: Physical, vol. 273, pp. 121-133, Apr. 2018.

Holbek et al., "Volumetric 3-D vector flow measurements using a 62+62 row-column-addressed array"; 2017 IEEE International Ultrasonics Symposium (IUS), Sep. 2017.

Hooley et al., "Breast Ultrasonography: State of the Art"; Radiology vol. 268, No. 3, Sep. 2013.

Moore et al., "Shape sensing using multi-core fiber optic cable and parametric curve solutions"; Optics Express, vol. 20, Issue 3, pp. 2967-2973 (2012), Jan. 2012.

Ophir et al., "Elastography: Imaging the elastic properties of soft tissues with ultrasound"; Journal of Medical Ultrasonics, vol. 29, Dec. 2002.

Pietrangelo et al., "Does 'Breast Cancer Bra' Really Work?"; https://www.healthline.com/health-news/does-breast-cancer-bra-really-work, May 2017.

Zanotel et al., "Automated breast ultrasound: basic principles and emerging clinical applications"; La Radiologia Medica, vol. 123, Issue 1, pp. 1-12, Jan. 2018.

Notice of Allowance dated Jul. 7, 2023, for U.S. Appl. No. 16/658,237; 19 pages.

Restriction Requirement dated Apr. 19, 2022, for U.S. Appl. No. 16/658,237; 7 pages.

Response to Restriction Requirement dated Apr. 19, 2022, for U.S. Appl. No. 16/658,237; Response filed Apr. 28, 2022; 1 page.

Non-Final Office Action dated May 12, 2022, for U.S. Appl. No. 16/658,237; 21 pages.

Response to Non-Final Office Action dated May 12, 2022, for U.S. Appl. No. 16/658,237; Response filed Aug. 11, 2022; 11 pages.

Final Office Action dated Nov. 25, 2022, for U.S. Appl. No. 16/658,237; 20 pages.

Response to Final Office Action dated Nov. 25, 2022, for U.S. Appl. No. 16/658,237; Response filed Feb. 27, 2023; 11 pages.

Request for Continued Examination (RCE) dated Feb. 27, 2023, for U.S. Appl. No. 16/658,237; 3 pages.

Restriction Requirement dated Apr. 12, 2024, for U.S. Appl. No. 18/458,406; 6 pages.

Response to Restriction Requirement dated Apr. 12, 2024, for U.S. Appl. No. 18/458,406; Response filed May 16, 2024; 1 page.

Non-Final Office Action dated Jun. 6, 2024, for U.S. Appl. No. 18/458,406; 15 pages.

Response to Non-Final Office Action dated Jun. 6, 2024, for U.S. Appl. No. 18/458,406; Response filed Aug. 8, 2024; 7 pages.

Notice of Allowance dated Aug. 28, 2024, for U.S. Appl. No. 18/458,406; 10 pages.

U.S. Appl. No. 19/504,611, filed Jan. 22, 2026, Dagdeviren.

EP 2263808 23 Pages, Dec. 22, 2010, Galluzzo, et al.

WO 2006/040597 76 Pages, Apr. 20, 2006, Luebcke.

WO 2012/077111 A1 84 Pages, Jun. 14, 2012, Berman.

Akram, et al.; "Awareness and current knowledge of breast cancer"; Biological Research, vol. 50, No. 33; 2017; 23 pages.

Alkilani, et al.; "Transdermal Drug Delivery: Innovative Pharmaceutical Developments Based on Disruption of the Barrier Properties of the stratum corneum"; Pharmaceutics; vol. 7; Oct. 22, 2015; 33 Pages.

American Cancer Society; "Understanding a Breast Cancer Diagnosis"; https://www.cancer.org/cancer/types/breast-cancer/understanding-a-breast-cancer-diagnosis.html; Nov. 8, 2021; 42 pages.

Ameultrasounds.com; "GE ML6-15-D Ultrasound Transducer"; https://ameultrasounds.com/products/ge-ml6-15-d-linear-array-probe; Jan. 9, 2026; 5 pages.

Amiri, et al.; "Experimentally verified finite element modeling and analysis of a conformable piezoelectric sensor"; Smart Material and Structures; vol. 30; 2021; 31 Pages.

Andersen, et al.; "Simulation of Piezoelectric Transformers with COMSOL"; 2012; 7 Pages.

Arora, et al.; "Needle-free delivery of macromolecules across the skin by nanoliter-volume pulsed microjets"; PNAS; vol. 104, No. 11; pp. 4255-4260; Mar. 13, 2007; 6 Pages.

Ashokkumar; "The Characterization of acoustic cavitation bubbles—an overview"; Ultrasonics Sonochemistry; vol. 18; 2011; 9 Pages.

Barger; "Thresholds of Acoustic Cavitation"; Office of Naval Research; Acoustics Research Laboratory; Technical Memorandum; No. 57; Apr. 1964; 204 Pages.

Barry; "Novel mechanisms and devices to enable successful transdermal drug delivery"; European Journal of Pharmaceutical Sciences; vol. 14; Accepted Jun. 14, 2001; 14 Pages.

Ben Daya, et al.; "Compensated Row-Column Ultrasound Imaging System Using Multilayered Edge Guided Stochastically Fully Connected Random Fields"; Scientific Reports; vol. 7; Sep. 6, 2017; 18 Pages.

Bhatnagar, et al.; "Exploitation of sub-micron cavitation nuclei to enhance ultrasound-mediated transdermal transport and penetration of vaccines"; Journal of Controlled Release; vol. 238; Available Jul. 12, 2016; 9 Pages.

Blaber, et al. "Ncorr: Open-Source 2D Digital Image Correlation Matlab Software"; Experimental Mechanics; Published online Mar. 31, 2015; 18 Pages.

Boucaud, et al.; "Effect of Sonication parameters on transdermal delivery of insulin to hairless rats"; Journal of Controlled Release; vol. 81; Accepted Feb. 20, 2002; 7 Pages.

Boucaud, et al.; "In Vitro Study of low-frequency ultrasound-enhanced transdermal transport of fentanyl and caffeine across human and hairless rat skin"; International Journal of Pharmaceutics; vol. 228; Accepted Jul. 10, 2001; 9 Pages.

Bouzari, et al.; "Volumetric Ultrasound Imaging with Row-Column Addressed 2-D Arrays Using Spatial Matched Filter Beamforming"; 2015 IEEE International Ultrasonics Symposium Proceedings; 2015; 4 Pages.

Brem, et al.; "Screening Breast Ultrasound: Past, Present, and Future"; American Journal of Roentgenology; vol. 204; Feb. 2015; 7 Pages.

Burt, et al.; "Think Multi-Site Sensors for Continuous Body Temperature Measurement"; Maximum Integrated; 2014; 9 Pages.

Bu, et al.; "Measuring Muscle Movements for Human Interfaces Using a Flexible Piezoelectric Thin Film Sensor"; 30th Annual International Conference of the IEEE Engineering in Medicine and Biology Society; Aug. 20-24, 2008; 5 Pages.

(56)          References Cited

OTHER PUBLICATIONS

Caupin, et al.; "Cavitation in water: a review"; Science Direct—C. R. Physique; vol. 7; 2006; 18 Pages.

Chantasart, et al.; "Structure Enhancement Relationship of Chemical Penetration Enhancers in Drug Transport Across the Stratum Corneum"; vol. 4; Jan. 17, 2012; 22 Pages.

Chen, et al. "Smart Clothing: Connecting Human with Clouds and Big Data for Sustainable Health Monitoring"; Mobile Networks and Applications, vol. 21; Jul. 7, 2016; 21 Pages.

Chorsi, et al.; "Piezoelectric Biomaterials for Sensors and Actuators"; Advanced Materials, vol. 31, 2019; 15 pages.

Cianfrocca, et al.; "Prognostic and Predictive Factors in Early-Stage Breast Cancer"; The Oncologist, vol. 9, No. 6; May 21, 2004; 11 pages.

CTS Corporation; "PZT Materials Complete Properties" https://www.ctscorp.com/wp-content/uploads/CTS-Piezoelectric-Material-Properties Full-List_July21.pdf, Jul. 26, 2021; 5 Pages.

Cummins, et al.; "High-Frequency Ultrasound Array Designed for Ultrasound-Guided Breast Biopsy"; IEEE Transactions on Ultrasonics, Ferroelectrics, and Frequency Control; vol. 63, No. 6; Jun. 2016; 11 Pages.

Cummins, et al.; "High-Frequency ultrasound imaging for breast cancer biopsy guidance"; Journal of Medical Imaging; vol. 2, No. 4; Published online Dec. 10, 2015; 10 Pages.

Cu, et al.; "Delivery Strategies for Skin: Comparison of Nanoliter Jets, Needles and Topical Solutions"; Annals of Biomedical Engineering; vol. 48, No. 7; Jul. 2020; 12 Pages.

Dagdeviren, et al.; "Conformable amplified lead zirconate titanate sensors with enhanced piezoelectric response for cutaneous pressure monitoring"; Nature Communications; Aug. 5, 2014; 10 Pages.

Dagdeviren, et al.; "Conformal piezoelectric systems for clinical and experimental characterization of soft tissue"; Nature Materials; vol. 14; Jul. 2015; 11 Pages.

Dagdeviren, et al.; "Energy Harvesting from the Animal/Human Body for Self-Powered Electronics"; Annual Review of Biomedical Engineering, vol. 19; 2017; 27 pages.

Dagdeviren, et al.; "Flexible piezoelectric devices for gastrointestinal motility sensing"; Nature Biomedical Engineering, vol. 1; Oct. 2017; 11 pages.

Dagdeviren, et al.; "Recent Progress in flexible and stretchable piezoelectric devices for mechanical energy harvesting, sensing and actuation"; Extreme Mechanics Letters; vol. 9; Available Online Jun. 11, 2016; 13 Pages.

Denet et al.; "Skin Electroporation for transdermal and topical delivery"; Elsevier—Advanced Drug Delivery Reviews; pp. 659-674; 2004; 16 Pages.

DePolo; "Breast Cancer Stages"; https://www.breastcancer.org/pathology-report/breast-cancer-stages; Jul. 15, 2025; 9 pages.

Dhand, et al.; "Role of Size of Drug Delivery Carriers in Pulmonary and Intravenous Administration with Emphasis on Cancer Therapeutics and Lung-Targeted Drug Delivery"; RSC Advances; vol. 4; No. 62; 2014; 39 Pages.

Dharadhar, et al.; "Microneedles for transdermal drug delivery: a systematic review"; Drug Development and Industrial Pharmacy; Nov. 27, 2018; 15 Pages.

Diab, et al.; "Engineered Nanoparticulate Drug Delivery Systems: The Next Frontier for Oral Administration?"; The AAPS Journal; vol. 14, No. 4; Published Online Jul. 6, 2012; 15 Pages.

Durmus, et al.; "Is phonophoresis effective in the treatment of chronic low back pain? A single-blind randomized controlled trial"; Rheumatol Int.; vol. 33; pp. 1737-1744; Jan. 3, 2013; 8 Pages.

Du, et al.; "Conformable ultrasound breast patch for deep tissue scanning and imaging"; Science Advances, vol. 9; Jul. 28, 2023; 13 pages.

Eddings, et al.; "Determining the optimal PDMS-PDMS bonding technique for microfluidic devices"; Journal of Micromechanics and Microengineering; vol. 18; Apr. 25, 2008; 4 Pages.

Engholm, et al.; "Probe Development of CMUT and PZT row-column-addressed 2-D arrays"; Sensors and Actuators; vol. 273; Available Online Feb. 21, 2018; 13 Pages.

Esposito, et al.; "A Piezoresistive Sensor to Measure Muscle Contraction and Mechanomyography"; Sensors; vol. 18; Aug. 4, 2018; 12 Pages.

Fernandez, et al.; "On-Body Piezoelectric Energy Harvesters through Innovative Designs and Conformable Structures"; ACS Biomaterials Science & Engineering; Oct. 21, 2021; 17 pages.

Fernandez, et al.; "Ubiquitous conformable systems for imperceptible computing"; Foresight; Accepted Mar. 26, 2021; 24 Pages.

Gaertner; "Frequency Dependence of Ultrasonic Cavitation"; The Journal of the Acoustic Society of America; vol. 26, No. 5; Nov. 1954; 4 Pages.

Galloway; "An Experimental Study of Acoustically Induced Cavitation in Liquids"; The Journal of the Acoustical Society of America; vol. 26, No. 5; Sep. 1954; 9 Pages.

Guo, et al.; "Ultrasound Imaging Technologies for Breast Cancer Detection and Management: A Review"; 2017; 76 pages.

Hakozaki, et al.; "Ultrasound enhanced skin-lightening effect of vitamin C and niacinamide"; Skin Research and Technology; p. 105-113; 2006; 9 Pages.

Hedrick, et al.; "Beam Steering and Focusing With Linear Phased Arrays"; Journal of Diagnostic Medical Sonography, vol. 12,; pp. 211-215; Sep./Oct. 1996; 5 pages.

Holbek, et al.; "Volumetric 3-D Vector Flow Measurements using a 62+62 Row-Column Addressed Array"; IEEE International Ultrasonics Symposium; 2017; 4 Pages.

Hooley, et al.; "Breast Ultrasonography: State of the Art"; Radiology; vol. 268, No. 3; Sep. 2013; 18 Pages.

Hughes-Riley, et al.; "A Study of Thermistor Performance Within a Textile Structure"; Sensors; vol. 17; Aug. 5, 2017; 14 Pages.

Hu, et al.; "Stretchable ultrasonic transducer arrays for three-dimensional imaging on complex surfaces"; Science Advances, vol. 4; Mar. 23, 2018; 11 pages.

Hu, et al.; "A wearable cardiac ultrasound imager"; Nature, vol. 613; Jan. 26, 2023; 23 pages.

Iizuka, et al.; "A New Flexible Piezoelectric Pressure Sensor Array for The Noninvasive Detection of Laryngeal Movement During Swallowing"; The Journal of Physiological Sciences; vol. 68; Mar. 5, 2018; 10 Pages.

Iliopoulos, et al.; "Franz Cell Diffusion Testing and Quantitative Confocal Raman Spectroscopy: In Vitro-In Vivo Correlation"; Pharmaceutics; Sep. 18, 2020; 12 Pages.

Iliopoulos, et al.; "Topical Delivery of niacinamide: Influence of neat solvents"; International Journal of Pharmaceutics: vol. 579; Available Online Feb. 11, 2020; 8 Pages.

Jensen; "Medical ultrasound imaging"; Progress in Biophysics and Molecular Biology, vol. 93; 2007; 13 pages.

Johnston; "The Cavitation subharmonic signal: mechanistic source and optimized detection"; Doctoral dissertation; University of Dundee; 2016; Part 1; 100 Pages.

Johnston; "The Cavitation subharmonic signal: mechanistic source and optimized detection"; Doctoral dissertation; University of Dundee; 2016; Part 2; 98 Pages.

Jones; "The Application of Temperature Sensors into Fabric Substrates"; Master's Thesis, Kansas State University; 2011; 90 Pages.

Jung, et al.; "Diffusion properties of different compounds across various synthetic membranes using Franz-type diffusion cells"; Journal of Pharmaceutical Investigation; vol. 42; pp. 271-277; Oct. 8, 2012; 7 Pages.

Jung, et al.; "Effect of Ultrasound and heat on percutaneous absorption of L-ascorbic acid: human in vitro studies on Franz cell and Petri dish systems"; International Journal of Cosmetic Science; vol. 38; pp. 646-650; Accepted Jul. 2, 2016; 5 Pages.

Kalantarian, et al.; "Monitoring Eating Habits Using a Piezoelectric Sensor-Based Necklace"; Computers in Biology and Medicine, vol. 58; pp. 46-55; Accepted Jan. 1, 2015; 10 Pages.

Kalia, et al.; "Iontophoretic drug delivery"; Advanced Drug Delivery Reviews; vol. 56; pp. 619-658; 2004; 40 Pages.

Kang, et al.; "The lint of an IMU Integrated Clothes for Postural Monitoring Using Conductive Yarn and Interconnecting Technology"; Sensors; vol. 17; Nov. 7, 2017; 10 Pages.

(56)             References Cited

OTHER PUBLICATIONS

Kerboua, et al.; "Void Fraction number density of acoustic cavitation bubbles, and acoustic frequency: A numerical investigation"; The Journal of the Acoustical Society of America; vol. 146, No. 4; Oct. 2019; 13 Pages.

Kim, et al.; "Characterization of Electrical Heating of Graphene/PLA Honeycomb Structure Composite Manufactured by CFDM 3D Printer"; Fashion and Textiles, vol. 7, No. 8; 2020; 18 pages.

Kolb, et al.; "Comparison of the Performance of Screening Mammography, Physical Examination, and Breast Us and Evaluation of Factors that Influence Them: An Analysis of 27,825 Patient Evaluations"; Radiology, vol. 225, pp. 165-175; 2002; 11 pages.

Kratkiewicz, et al.; "Ultrasound and Photoacoustic Imaging of Breast Cancer: Clinical Systems, Challenges, and Future Outlook"; Journal of Clinical Medicine, vol. 11; Feb. 22, 2022; 19 pages.

Krizek, et al.; "Repetitive regime of highly focused liquid microjets for needle-free injection"; Scientific Reports; Nature Research; vol. 10; 2020; 9 Pages.

Kuhl, et al.; "Mammography, Breast Ultrasound, and Magnetic Resonance Imaging for Surveillance of Women at High Familial Risk for Breast Cancer"; Journal of Clinical Oncology, vol. 23, No. 33; Nov. 20, 2005; 8 pages.

Lee, et al; "Dissolving Microneedles for Transdermal Drug Delivery"; Biomaterials; vol. 29, No. 13; pp. 2113-2124; May 2008; 23 Pages.

Lee, et al.; "Short Ultrasound Exposure Times for Noninvasive Insulin Delivery in Rats Using the Lightweight Cymbal Array"; IEEE Transactions on Ultrasonics, Ferroelectrics, and Frequency Control; vol. 51; No. 2; Feb. 2004; 5 Pages.

Lee, et al.; "Thickness-Dependent Properties of Relaxor-PbTiO$_3$ Ferroelectrics for Ultrasonic Transducers"; Advanced Functional Materials, vol. 20, No. 18; Sep. 23, 2010; 23 pages.

Liao, et al.; "Low-Frequency Dual-Frequency Ultrasound-mediated microbubble cavitation for transdermal minoxidil delivery and hair growth enhancement"; Scientific Reports; Nature Research; vol. 10; 2020; 12 Pages.

Lima, et al.; "Application of Imaging Technologies in Breast Cancer Detection: A Review Article"; Open Access Macedonian Journal of Medical Sciences, vol. 7, No. 5; pp. 838-848; Mar. 14, 2019; 11 pages.

Linz, et al. "Fully Integrated EKG Shirt based on Embroidered Electrical Interconnections with Conductive Yarn and Miniaturized Flexible Electronics"; Proceeding of the International Workshop on wearable and Implantable Body Sensor Networks; 2006; 4 Pages.

Lin, et al.; "Influence of domain size on the scaling effects in Pb(Mg1/3Nb2/3)O3—PbTiO3 ferroelectric crystals"; Scripta Materialia; vol. 64, No. 12; Jun. 2011; 10 pages.

Lin, et al.; "Soft wearable devices for deep-tissue sensing"; Nature Reviews Materials, vol. 7; Nov. 2022; 20 pages.

Liu, et al.; "Achieving Giant Piezoelectricity and High Property Uniformity Simultaneously in a Relaxor Ferroelectric Crystal through Rare-Earth Element Doping"; Advanced Science, vol. 9; 2022; 10 pages.

Liu, et al.; "Lab-On-Skin: A Review of Flexible and Stretchable Electronics for Wearable Health Monitoring"; American Chemical Society Nano; vol. 11; pp. 9614-9635; Sep. 1, 2017; 22 Pages.

Li, et al.; "Atomic-scale origin of ultrahigh piezoelectricity in samarium-doped PMN-PT ceramics"; Physical Review B, vol. 101; Apr. 27, 2020; 7 pages.

Li, et al.; "Review—Recent Progress in Flexible and Stretchable Piezoresistive Sensors and Their Applications"; Journal of the Electrochemical Society; vol. 167; Feb. 3, 2020; 22 Pages.

Li, et al.; "Stretchable Electronic Facial Masks for Sonophoresis"; American Chemical Society Nano; Mar. 29, 2022; 14 Pages.

Li, et al.; "Transdermal Delivery of Therapeutic Compounds With Nanotechnological Approaches in Psoriasis"; Frontiers in Bioengineering and Biotechnology; vol. 9; Article 804415; Jan. 24, 2022; 29 Pages.

Lukasiewicz, et al.; "Breast Cancer—Epidemiology, Risk Factors, Classification, Prognostic Markers, and Current Treatment Strategies—An Updated Review"; Cancers, vol. 13; Aug. 25, 2021; 30 pages.

Luo, et al.; "Emerging integrated nanohybrid drug delivery systems to facilitate the intravenous-to-oral switch in cancer chemotherapy"; Journal of Controlled Release; vol. 176; pp. 94-103; Available online Jan. 2, 2014; 10 Pages.

Luo et al.; "Technology Roadmap for Flexible Sensors"; ACS Nano, vol. 17, No. 6; Mar. 28, 2023; 171 pages.

Luzuriaga, et al.; "Biodegradable 3D Printed Polymer Microneedles for Transdermal Drug Delivery"; Lab on a Chip; Scholarone Manuscripts; Mar. 2, 2018; 10 Pages.

Machet, et al.; "Transdermal Transport by Sonophoresis"; Percutaneous Absorption—CRC Press; Chapter 43; 2021; 20 Pages.

Maione, et al.; "Transducer Design for a Portable Ultrasound Enhanced Transdermal Drug-Delivery System"; IEEE Transactions on Ultrasonics, Ferroelectrics, and Frequency Control; vol. 49, No. 10; Oct. 2002; 7 Pages.

Majumder, et al. "Wearable Sensors for Remote Health Monitoring" Sensors; vol. 17, No. 130; Jan. 12, 2017; 45 Pages.

Mance, et al.; "The influence of size, depth and histologic characteristics of invasive ductal breast carcinoma on thermographic properties of the breast"; Excli Journal, vol. 18; pp. 549-557; Jul. 22, 2019; 9 pages.

Manikkath, et al.; "Influence of peptide dendrimers and sonophoresis on the transdermal delivery of ketoprofen"; International Journal of Pharmaceutics; vol. 521; pp. 110-119; Available Online Feb. 2, 2017; 10 Pages.

Mattana, et al. "Woven Temperature and Humidity Sensors on Flexible Plastic Substrates for E-Textile Applications"; IEEE Sensors Journal; vol. 13; No. 10; Oct. 2013; 9 Pages.

Medicsen; "The Painless Alternate to manage Chronic Pain"; https://medicsen.com/en/; 2023; 11 pages.

Merino, et al.; "Frequency and thermal effects on the enhancement of transdermal transport by sonophoresis"; Journal of Controlled Release; vol. 88; pp. 85-94; 2003; 10 Pages.

Mirvakili, et al.; "Wireless on-demand drug delivery"; Nature Electronics; vol. 4; Jul. 2021; 14 Pages.

Mitragotri, et al.; "Determination of threshold energy dose for ultrasound-induced transdermal drug transport"; Journal of Controlled Release; vol. 63; pp. 41-52; 2000; 12 Pages.

Mitragotri; "Effect of therapeutic ultrasound on partition and diffusion coefficients in human stratum corneum"; Journal of Controlled Release; vol. 71; 2001; 7 Pages.

Mitragotri, et al.; "Low-Frequency Sonophoresis: A Noninvasive Method of Drug Delivery and Diagnostics"; Biotechnol. Prog. vol. 16, No. 3 ; 2000; 5 Pages.

Mitragotri, et al.; "Transdermal Delivery of Heparin and Low-Molecular Weight Heparin Using Low-Frequency Ultrasound"; Pharmaceutical Research; vol. 18; No. 8; Accepted May 3, 2001; 6 Pages.

Mitragotri, et al.; "Transdermal Drug Delivery Using Low-Frequency Sonophoresis"; Pharmaceutical Research; vol. 13, No. 3; 1996; 10 Pages.

Mitragotri, et al.; "Ultrasound-Mediated Transdermal Protein Delivery"; Science; New Series; vol. 269, No. 5225; pp. 850-853; Aug. 11, 1995; 5 Pages.

Moore, et al.; "Shape Sensing Using Multi-Core fiber optic cable and parametric curve solutions"; Optics Express; vol. 20, No. 3; Jan. 30, 2012; 7 Pages.

N A Hadi, et al; "Experimental Study of the Characteristics of Acoustic Cavitation Bubbles Under the Influence of Ultrasonic Wave"; IOP Conference Series: Materials Science and Engineering; vol. 808; 2020; 9 Pages.

Nguyen, et al.; "Dependence of cavitation, chemical effect, and mechanical effect thresholds on ultrasonic frequency"; Ultrasonics—Sonochemistry; vol. 39; Available online Apr. 27, 2017; 6 Pages.

Nguyen, et al.; "Tactile Imaging of an Imbedded Palpable Structure for Breast Cancer Screening"; ACS Applied Materials & Interfaces, vol. 6; pp. 16368-16374; Aug. 22, 2014; 7 pages.

Nowicki; "Safety of ultrasonic examinations; thermal and mechanical indices"; Medical Ultrasonography, vol. 22; No. 2; pp. 203-210; 2020; 8 pages.

(56) References Cited

OTHER PUBLICATIONS

Oberli, et al.; "Ultrasound-enhanced transdermal delivery: recent advances and future challenges"; Therapeutic Delivery; vol. 5, No. 7; 2014; 15 Pages.

Oh, et al.; "Effect of Mn on Dielectric and Piezoelectric Properties of 71PMN-29PT [71Pb(Mg1/3Nb2/3)O3—29PbTiO3] Single Crystals and Polycrystalline Ceramics."; Journal of the Korean Ceramic Society, vol. 55, No. 2; pp. 166-173; Accepted Feb. 13, 2018; 8 pages.

Olfatnia, et al.; "Medium damping influences on the resonant frequency and quality factor of piezoelectric circular microdiaphragm sensors"; Journal of Micromechanics and Microengineering; vol. 21; 2011; 10 Pages.

Ophir, et al.; "Elastography: Imagine the Elastic Properties of Soft Tissues with Ultrasound"; J Med Ultrasonics; vol. 29; Accepted Sep. 13, 2022;17 Pages.

Ou et al.; "SensorKnit: Architecting Textile Sensors with Machine Knitting"; 3D Printing and Additive Manufacturing; vol. 6; No. 1; Mar. 2019; 11 Pages.

Oxsonics; Cancer. This time you're going to listen; https://oxsonics. com/; 2018; 5 Pages.

Paliwal, et al.; "Low-frequency Sonophoresis: Ultrastructural Basis for Stratum Corneum Permeability Assessed Using Quantum Dots"; The Society for Investigative Dermatology; Mar. 9, 2006; 7 Pages.

Pan, et al.; "Two-Dimensional Digital Image Correlation for In-Plane Displacement and Strain Measurement: A Review"; Measurement Science and Technology; vol. 20; 2009; 18 Pages.

Paradiso, et al.; "Textile Electrodes and Integrated Smart Textile for Reliable Biomonitoring"; 2011 Annual International Conference of the IEEE Engineering in Medicine and Biology Society; Aug. 2011; 4 Pages.

Park, et al.; "Enhanced Transdermal Drug Delivery by Sonophoresis and Simultaneous Application of Sonophoresis and Iontophoresis"; AAPS PharmSciTech; vol. 20; Jan. 29, 2019; 7 Pages.

Park, et al.; "Sonophoresis with ultrasound-responsive liquid-core nuclei for transdermal drug delivery"; Skin Res. Technol. vol. 28; Accepted Dec. 18, 2021; 8 Pages.

Paul, et al. "A Smart Textile Based Facial EMG and EOG Computer Interface"; IEEE Sensors Journal; vol. 14; No. 2; Feb. 2014; 8 Pages.

Pham, et al.; "Chemical penetration enhancers in stratum corneum—Relation between molecular effects and barrier function"; Journal of Controlled Release; vol. 232; Available Apr. 22, 2016; 13 Pages.

Pietrangelo; "Does 'Breast Cancer Bra' Really Work?"; Health News; May 18, 2017; http://www.healthline.com/health-news/does-breast-cancer-bra-realy-work#6; 6 Pages.

Piezo.com; "Materials Technical Data (Typical Values)"; https:/info. piezo.com/hubfs/Data-Sheets/piezo-material-properties-data-sheet-20201112.pdf; 1 page.

Polat, et al.; "Low-Frequency Sonophoresis: Application to the Transdermal Delivery of Macromolecules and Hydrophilic Drugs"; Expert Opin Drug Deliv.; vol. 7, No. 12; pp. 1415-1432; Dec. 2010; 29 Pages.

Polat, et al.; "Ultrasound-Mediated Transdermal Drug Delivery: Mechanisms, Scope, and Emerging Trends"; J Control Release; vol. 152, No. 3; Jun. 30, 2011; 49 Pages.

Prausnitz, et al.; "Current Status and Future Potential of Transdermal Drug Delivery"; Nature Reviews; vol. 3; Feb. 2004; 10 Pages.

Prausnitz; "Microneedles for transdermal drug delivery"; Advanced Drug Delivery Reviews; vol. 56; 2004; 7 Pages.

Prausnitz, et al.; "Transdermal Drug Delivery"; Nature Biotechnology; vol. 26, No. 11; Nov. 2008; 8 Pages.

Qi; "Design and Safety Assessment of Wearable Transcranial Low-Intensity Pulsed Ultrasound Devices"; Department of Electrical and Computer Engineering; University of Alberta; 2020; 100 Pages.

Rao, et al.; "Sonophoresis: recent advancements and future trends"; Journal of Pharmacy and Pharmacology; vol. 61; Accepted Mar. 2, 2009; 17 Pages.

Rella, et al.; "Automated Breast Ultrasonography (ABUS) in the Screening and Diagnostic Setting: Indications and Practical Use"; Article in Press; 2018; 14 pages.

Ren, et al.; "Recent Advances in Flexible Ultrasonic Transducers: From Materials Optimization to Imaging Applications"; Micromachines, vol. 14; Jan. 2, 2023; 21 pages.

Rich, et al.; "Relations between acoustic cavitation and skin resistance during intermediate- and high-frequency sonophoresis"; Journal of Controlled Release; vol. 194; pp. 266-277; Nov. 28, 2014; 32 Pages.

Robertson, et al.; "Influence of Acoustic Reflection on the Inertial Cavitation Dose in a Franz Diffusion Cell"; Ultrasound in Med. & Biol.; vol. 44, No. 5; Jan. 29, 2018; 10 Pages.

Rooze, et al.; "Dissolved gas and ultrasonic cavitation- a review"; Ultrasonics Sonochemistry; vol. 20; 2013; 11 Pages.

Ryu, et al. "A Knitted Glove Sensing System with Compression Strain for Finger Movements"; Smart Materials and Structures; vol. 27; 2018; 8 Pages.

Salvador, et al.; "Toward Accurate Dynamic Time Warping in Linear Time and Space"; Intelligent Data Analysis; vol. 11;pp. 561-580; Jun. 2, 2007; 20 Pages.

Sayem, et al.; "Review on Smart Electro-Clothing Systems (SeCSs)"; Mar. 15, 2019; 34 Pages.

Scheirer, et al.; "Expression Glasses: A Wearable Device for Facial Expression Recognition"; Late-Breaking Results; CHI 99; May 15-20, 1999; 2 Pages.

Schoellhammer, et al.; "Applicability and Safety of dual-frequency ultrasonic treatment for the transdermal delivery of drugs"; Journal of Controlled Release; Available Online Feb. 4, 2015; 8 Pages.

Seah, et al.; "Recent advances in ultrasound-based transdermal drug delivery"; International Journal of Nanomedicine; vol. 13; pp. 7749-7763; 2018; 15 Pages.

Segebarth, et al.; "Correlation between Acoustic Cavitation Noise, Bubble Population, and Sonochemistry"; J. Phys. Chem. B.; vol. 106; pp. 9181-9190; 2002; 10 Pages.

Shingade, et al.; "Review on: Recent Trend on Transdermal Drug Delivery System"; Journal of Drug Delivery & Therapeutics; vol. 2, No. 1; Available Online Jan. 20, 2012; 10 Pages.

Shin, et al.; "Current status of automated breast ultrasonography"; Ultrasonography, vol. 34, No. 3; Jul. 2015; 8 pages.

Singh, et al.; "Microneedling: Advances and widening horizons"; Indian Dermatology Online Journal; 2016; 11 Pages.

Sohn, et al.; "Primary tumor location impacts breast cancer survival"; The American Journal of Surgery, vol. 195; pp. 641-644; 2008; 4 pages.

Solav et al.; "Bone Pose Estimation in the Presence of Soft Tissue Artifact Using Triangular Cosserat Point Elements"; Annals of Biomedical Engineering; Accepted Jul. 2015; 22 Pages.

Solav, et al. "Chest Wall Kinematics Using Triangular Cosserat Point Elements in Healthy and Neuromuscular Subjects"; Annals of Biomedical Engineering, vol. 45, No. 8; Apr. 2017; 29 Pages.

Solav et al. "MultiDIC: An Open-Source Toolbox for Multi-View 3D Digital Image Correlation"; IEEE Access; Jun. 4, 2018; 16 Pages.

Sonotarg; https://sonotarg.com/technology/; Registered in Northern Ireland: N1656568; 2026; 3 Pages.

Stride, et al.; "Nucleation, Mapping and Control of Cavitation for Drug Delivery"; Nature Reviews Physics; vol. 1, No. 8; Jun. 17, 2019; 34 Pages.

Sun, et al.; "Decoding of facial strains via conformable piezoelectric interfaces"; Nature Biomedical Engineering, vol. 4; Oct. 2020; 22 pages.

Su, et al. "Nanoparticle Based Curve Arrays for Multirecognition Flexible Electronics"; Advanced Materials; vol. 28; pp. 1369-1374; 2016; 6 Pages.

Su; "Splitting of neutral mechanical plane of conformal multilayer piezoelectric mechanical energy harvester"; Applied Physics Letters; vol. 1, No. 7; Jul. 29, 2015; 5 Pages.

Tachibana, et al.; "Use of Ultrasound to Enhance the Local Anesthetic Effect of Topically Applied Aqueous Lidocaine"; Laboratory Investigations; American Society of Anesthesiologists, Inc.; vol. 78; pp. 1091-1096; 1993; 6 Pages.

(56) References Cited

OTHER PUBLICATIONS

Tamaddoni, et al.; "Acoustic Methods for Increasing the Cavitation Initiation Pressure Threshold"; IEEE Transactions on Ultrasonics, Ferroelectrics, and Frequency Control; vol. 65, No. 11; Nov. 2018; 8 Pages.

Tang, et al.; "Theoretical Description of Transdermal Transport of Hydrophilic Permeants: Application to Low-Frequency Sonophoresis"; Journal of Pharmaceutical Sciences; vol. 90, No. 5; May 2001; 24 Pages.

Tao, et al.; "Bluetooth Low Energy-Based Washable Wearable Activity Motion and Electrocardiogram Textronic Monitoring and Communicating System"; Advanced Materials Technology; vol. 3; 2018; 6 Pages.

Terahara, et al.; "Dependence of low-frequency sonophoresis on ultrasound parameters; distance of the horn and intensity"; International Journal of Pharmaceutics; vol. 235; pp. 35-42; 2002; 8 Pages.

Tezel, et al.; "Interactions of Inertial Cavitation Bubbles with Stratum Corneum Lipid Bilayers during Low-Frequency Sonophoresis"; Biophysical Journal; vol. 85; Dec. 2003; 11 Pages.

Trafton; "Wearable patch can painlessly deliver drugs through the skin"; MIT News on campus and around the world; https://news.mit.edu/2023/wearable-patch-can-painlessly-deliver-drugs-through-skin-0419; Apr. 19, 2023; 5 Pages.

Trolier-McKinstry, et al.; "High-Performance Piezoelectric Crystals, Ceramics, and Films"; Annual Review of Materials Research, vol. 48; Mar. 12, 2018; 27 pages.

Uchino; "The Development of Piezoelectric Materials and the New Perspective"; Advanced Piezoelectric Materials; Woodhead Publishing; 2017; 92 Pages.

Varatharajan, et al.; "Wearable Sensor Devices for Early Detection of Alzheimer Disease Using Dynamic Time Warping Algorithm"; Cluster Computing; vol. 21; 2018; 10 Pages.

Venkatesh, et al.; "Transdermal drug delivery system: An overview"; International Journal of Research in Pharmaceutical Sciences; Apr. 2012; 9 Pages.

Wang, et al.; "Continuous monitoring of deep-tissue haemodynamics with stretchable ultrasonic phased arrays"; Nature Biomedical Engineering, vol. 5; Jul. 2021; 15 pages.

Wang, et al.; "Flexible Doppler ultrasound device for the monitoring of blood flow velocity"; Science Advances, vol. 7; Oct. 27, 2021; 10 pages.

Wang, et al.; "Monitoring of the central blood pressure waveform via a conformal ultrasonic device"; Nature Biomedical Engineering, vol. 2; No. 9; Sep. 2018; 22 pages.

Wang, et al.; "Optimize multilayer matching layer design for tone-burst underwater acoustic transducers"; The Journal of the Acoustical Society of America; vol. 152; 2022; 10 Pages.

Wan, et al.; "Adaptive Cost Dynamic Time Warping Distance in Time Series Analysis for Classification"; Journal of Computational and Applied Mathematics; vol. 319; 2017; 7 Pages.

Xiong, et al. "Compression Garments for Medical Therapy and Sports"; Polymers; vol. 10; Jun. 14, 2018; 19 Pages.

Xue, et al.; "Development of a Wearable Ultrasound Transducer for Sensing Muscle Activities in Assistive Robotics Applications"; Biosensors; Jan. 13, 2023; 16 pages.

Yamashita, et al.; "Scanning Electron Microscopic Evaluation of the Skin Surface After Ultrasound Exposure"; The Anatomical Record; vol. 247; 1997; 7 Pages.

Yu, et al.; "A Conformable Ultrasound Patch for Cavitation-Enhanced Transdermal Cosmeceutical Delivery"; Advanced Materials; 2023; 16 pages.

Zanotel, et al.; "Automated Breast Ultrasound: basic principles and emerging clinical applications"; Springer; Breast Radiology; vol. 123; 2017; 12 Pages.

Zhang, et al.; "A continuous tri-phase transition effect for HIFU-mediated intravenous drug delivery"; Biomaterials; 2014; 11 Pages.

Zhang, et al.; "Dermal Delivery of Niacinamide—In Vivo Studies"; Pharmaceutics; May 14, 2021; 14 Pages.

Zhang, et al., "Dynamic Time Warping under Limited Warping Path Length"; Information Sciences; Available online Feb. 9, 2017; 17 Pages.

Zhang, et al.; "A Comparison of the in vitro permeation of niacinamide in mammalian skin and in the Parallel Artificial Membrane Permeation Assay (PAMPA) model"; Manuscript; 28 Pages.

Zhou, et al. "Expressure: Detect Expressions Related to Emotional and Cognitive Activities Using Forehead Textile Pressure Mechanomyography"; Sensors; Jan. 28, 2020; 22 Pages.

Zhou, et al.; "Piezoelectric single crystal ultrasonic transducers for biomedical applications"; Progress in Materials Science, vol. 66; Oct. 2014; 51 pages.

Zysset, et al.; "Textile Integrated Sensors and Actuators for Near-Infrared Spectroscopy"; Optics Express; vol. 21; No. 3; Published Feb. 11, 2013; 12 Pages.

Notice of Allowance dated Jul. 25, 2023, for U.S. Appl. No. 17/163,410; 9 pages.

Non-Final Office Action dated Jun. 7, 2023, for U.S. Appl. No. 17/163,410; 20 pages.

Response to Non-Final Office Action dated Jun. 7, 2023, for U.S. Appl. No. 17/163,410; Response filed Jul. 10, 2023; 12 pages.

International Search Report and Written Opinion dated Oct. 10, 2024 for International Patent Application No. PCT/US2024/029900; 11 pages.

Ahmad, et al.; "Interrelations Between Albuminuria, Electrocardiogramal Abnormality, and Incident Atrial Fibrillation in the Multi-Ethnic Study of Atherosclerosis (MESA) Cohort"; International Journal of Cardiology; vol. 383; pp. 102-109; Apr. 2023; 8 Pages.

Cserni, et al.; "The New TNM Based Staging of Breast Cancer"; Virchows Archive; Jan. 27, 2018; 7 Pages.

Essa, et al.; "The relationship between distance of breast cancer from the skin and incidence of axillary nodal metastasis in female patients with early cancer breast: correlation between radiological and pathological distance"; The Egyptian Journal of Surgery; vol. 40; 2021; 10 Pages.

Gao, et al.; "Piezoelectric Actuators and Motors: Materials, Designs, and Applications"; Advanced Materials Technologies; vol. 5; 2020; 26 Pages.

The Institute of Electrical of Electrical and Electronics Engineers, Inc.; "IEEE Standard on Piezoelectricity"; ANSI/IEEE Std; Part 1; 50 Pages.

The Institute of Electrical of Electrical and Electronics Engineers, Inc.; "IEEE Standard on Piezoelectricity"; ANSI/IEEE Std; 1988; Part 2; 24 Pages.

Kim, et al.; "Aspect ratio dependence of electromechanical coupling coefficient of piezoelectric resonators"; Applied Physics Letters; vol. 87; 2005; 4 Pages.

Lee, et al.; "Automated Conformal Ultrasound Scanning for Breast Screening"; Journal of Medical and Biological Engineering; vol. 38; pp. 116-128; 2018; 13 Pages.

Lin., et al.; "Characterization and piezoelectric thermal stability of PIN-PMN-PT ternary ceramics near the morphotropic phase boundary"; Journal of Alloys and Compounds; vol. 489; pp. 115-118; 2010; 4 Pages.

Li, et al.; "Enhanced Piezoelectric Properties and Improved Property Uniformity in Nd-Doped PMN-PT Relaxor Ferroelectric Single Crystals"; Advanced Functional Materials; vol. 32; 2022; 7 Pages.

Li, et al.; "Giant piezoelectricity of Sm-doped $Pb(Mg_{1/3}Nb_{2/3})O_3$—$PbTiO_3$ single crystals"; Science; vol. 364; pp. 264-268; Apr. 19, 2019; 5 Pages.

Long, et al; "Temperature-dependent structure and electromechanical properties of Er doped PMN-PT single crystal grown by modified Bridgman technique"; Journal of Alloys and Compounds; vol. 902; Jan. 19, 2022; 9 Pages.

Nasrabadi, et al.; "A comprehensive survey on non-invasive wearable bladder volume monitoring systems"; Medical & Biological Engineering & Computing; vol. 59; pp. 1373-1402; Jul. 14, 2021; 30 pages.

Panda, et al.; "Experimental and numerical modelling of mechanical properties of 3D printed honeycomb structures"; Measurement; vol. 116; pp. 495-506; 2018; 12 Pages.

(56) References Cited

OTHER PUBLICATIONS

Piezo.com; "Materials Technical Data (Typical Values)"; https://info.piezo.com/hubfs/Data-Sheets/piezo-material-properties-data-sheet 20201112; Nov. 12, 2020; 1 Page.

Song, et al.; "Composition and electrical properties characterization of a 5" diameter PIN-PMN-PT single crystal by the modified Bridgman method"; Journal of Alloys and Compounds; vol. 851; 2021; 10 pages.

Wang, et al.; "Bioadhesive ultrasound for long-term continuous imaging of diverse organs"; Science; vol. 377; pp. 517-523; Jul. 29, 2022; 7 Pages.

Wong, et al.; "Development of a 20-MHz wide-bandwidth PMN-PT single crystal phased-array ultrasound transducer"; Ultrasonics; vol. 73; pp. 181-186; 2017; 6 Pages.

Yang, et al.; "High frequency needle ultrasonic transducers based on Mn doped piezoelectric single crystal"; Journal of Alloys and Compounds; vol. 832; 2020; 8 Pages.

Yan, et al.; "Growth and electrical properties of Yb3+ A-site doped PMNT: Yb single crystal"; Journal of Physics and Chemistry of Solids; vol. 173; 2023; 8 Pages.

Zhang, et al.; "High performance ferroelectric relaxor—PbTiO3 single crystals: Status and perspective"; Journal of Applied Physics; vol. 111; Part 1; 2012; 30 pages.

Zhang, et al.; "High performance ferroelectric relaxor—PbTiO3 single crystals: Status and perspective"; Journal of Applied Physics; vol. 111; Part 2; 2012; 21 pages.

\* cited by examiner

METHODS AND APPARATUS FOR IMAGING WITH CONFORMABLE ULTRASOUND PATCH

CROSS REFERENCE TO RELATED APPLICATIONS

This application is a divisional of and claims benefit to U.S. patent application Ser. No. 18/458,406, filed Aug. 30, 2023, which is a continuation of and claims benefit to U.S. patent application Ser. No. 16/658,237, filed Oct. 21, 2019, which issued as U.S. Pat. No. 11,779,302, on Oct. 10, 2023, and which claims the benefit under 35 U.S.C. § 119 of U.S. Provisional Application No. 62/748,442 filed Oct. 20, 2018 (the "Provisional"). The contents of the above-referenced applications are hereby incorporated by reference in their entireties.

STATEMENT REGARDING FEDERALLY SPONSORED RESEARCH

This invention was made with government support under ECCS2044688 awarded by The National Science Foundation. The government has certain rights in the invention.

FIELD OF TECHNOLOGY

The present invention relates generally to ultrasound imaging.

SUMMARY

In illustrative implementations of this invention, an ultrasound device conforms to a surface of a curvilinear part of a human body. For instance, the curvilinear body part may comprise a breast, knee, shoulder, wrist, ankle, finger, finger joint, toe, or toe joint.

We sometimes call the ultrasound device a "patch". The ultrasound patch may touch and fit snugly against the skin throughout a large region, even though the surface of the skin is curved in that region. The patch may adhere to the skin due to Van der Waals forces, without any gel or adhesive.

The patch may capture ultrasound images of underlying tissue in the curvilinear body part. For instance, the patch may capture ultrasound images of tissue in a large portion of a woman's breast. The ultrasound images may be analyzed to detect pathological conditions, such as cancer and other soft tissue diseases. The ultrasound images may each be a 3D image of a volume of tissue.

The patch may comprise a flexible elastomeric substrate, in which phased arrays of rigid piezoelectric ultrasound transducers are embedded. The phased arrays may transmit an ultrasound beam into tissue and may measure ultrasound echoes that reflect from the tissue. The measurements taken by the phased arrays may be processed, to create an ultrasound image of the tissue.

The phased arrays may steer ultrasound beams through a wide angle to image a volume of tissue. For instance, each phased array may transmit an ultrasound beam and may steer this beam through a large (e.g., 120 degree) angle, thereby imaging a much larger volume than would be possible if the phased array were to emit a beam in only one fixed direction.

In illustrative implementations, localization is performed to determine the 3D position of the phased arrays. This is desirable, because the 3D positions of the phased arrays would otherwise be unknown, due to elastic deformation of the flexible substrate when it conforms to the skin of a curved body part. To detect the 3D spatial position of a given phased array of the patch, three ultrasound transducers in a ring array in the patch may emit ultrasound pulses at different times. How long it takes for the pulses to reach the given phased array may be measured. Three distances may be calculated: (a) a first distance between the first ultrasound transducer in the ring array and the given phased array; (b) a second distance between the second ultrasound transducer in the ring array and the given phased array; and (c) a third distance between the third ultrasound transducer in the ring array and the given phased array. The 3D position of the given phased array may be calculated as the intersection of three spheres, where: (a) the first sphere is centered on the first transducer and has a radius equal to the first distance; (a) the second sphere is centered on the second transducer and has a radius equal to the second distance; and (c) the third sphere is centered on the third transducer and has a radius equal to the third distance.

Each phased array may independently capture data regarding a volume of tissue (e.g., image the volume). The different volumes of tissue that are measured by the different phased arrays may partially overlap and may together comprise a target region. In many implementations, each phased array takes measurements of only a portion of the target region. Data that encodes measurements taken by the different phased arrays (or that encodes images captured by the different phased arrays) may be fed as input into a reconstruction algorithm. The 3D positions of the phased arrays (detected by localization) may also be fed as input to the reconstruction algorithm. The reconstruction algorithm may output a 3D image of the entire volume of the target region.

In some cases, the ultrasound patch captures accurate, "single shot" images of the tissue in real time. This may enable the patch to capture accurate 3D images of soft tissue (e.g., a breast), even if the soft tissue shifts position between the images.

Stress and strain may occur at interfaces between rigid phased arrays and more flexible regions of the patch. It is desirable to reduce this stress and strain, in order to prevent the patch from being damaged (e.g., to prevent mechanical failure at these interfaces).

In illustrative implementations, this stress and strain is reduced by partially encapsulating each rigid phased array in an intermediate layer. Specifically, in some cases, each phased array is surrounded (except on its top side) by an intermediate layer. The intermediate layer may be located between the phased array and flexible substrate of the patch. The intermediate layer may comprise a semi-flexible material that is more flexible than the phased array and is less flexible than the substrate. The intermediate layer may tend to distribute stress that would otherwise be localized at an interface between the rigid phased array and the flexible substrate. In some cases, the intermediate layer comprises polydimethylsiloxane (PDMS). In some cases, the intermediate layer comprises silicone rubber or a polymeric foam (e.g., polystyrene foam or polyurethane foam). In some cases, the intermediate layer has a Young's modulus that is greater than or equal to 60 kPa and less than or equal to 2 GPa.

In some implementations, each phased array includes, among other things: (a) a flexible substrate; (b) a "matching" layer and "backing" layer; and (c) an array of piezoelectric ultrasound transducers.

The array of piezoelectric transducers may be arranged in rows and columns. A first set of electrodes may connect to the rows. A second set of electrodes may connect to the columns.

In some implementations, the first and second sets of the electrodes (which connect to the rows and columns, respectively) both connect to the transducer array at the same vertical height, albeit from different sides of the array. This spatial arrangement of the electrode connections may have at least three advantages. First, it may simplify fabrication of the phased array. Second, it may reduce the size of a phased array. Third, it may reduce signal processing complexity.

The ultrasound signal transmitted by the patch may tend to increase the temperature of the tissue being imaged. In illustrative implementations, this thermal effect is greatly reduced (and kept within safe levels) by at least two features of the ultrasound patch. First, in a given phased array, the transducers may pulse in temporal sequence, so that only one row or one column of the transducers in the array is pulsing at a time. Second, the phased arrays may be embedded in the flexible substrate of the patch in such a way that they are spatially separated from each other and thus are thermally isolated from each other. For instance, the distance between neighboring pairs of phased arrays may be much greater (e.g., at least two or three times greater) than the maximum dimension of a single phased array.

In some implementations, data gathered by the ultrasound patch is transmitted wirelessly, enabling the data to be processed remotely (by a remote computer) and interpreted remotely (e.g., by a remote physician who views and interprets the resulting ultrasound images).

In some use scenarios of this invention, a set of ultrasound patches captures a large number of 3D images of tissue of many patients. These images may be employed to train a neural network. After the neural network is trained, it may analyze a new 3D image captured by an ultrasound patch, in order to detect a pathological condition that is shown in the new image.

The Summary and Abstract sections and the title of this document: (a) do not limit this invention; (b) are intended only to give a general introduction to some illustrative implementations of this invention; (c) do not describe all of the details of this invention; and (d) merely describe non-limiting examples of this invention. This invention may be implemented in many other ways. Likewise, the Field of Technology section is not limiting; instead it identifies, in a general, non-exclusive manner, a field of technology to which some implementations of this invention generally relate.

The above Figures are not necessarily drawn to scale. The above Figures show illustrative implementations of this invention, or provide information that relates to those implementations. The examples shown in the above Figures do not limit this invention. This invention may be implemented in many other ways.

DETAILED DESCRIPTION

Conformable Ultrasound Patch

Figures 1, 2:
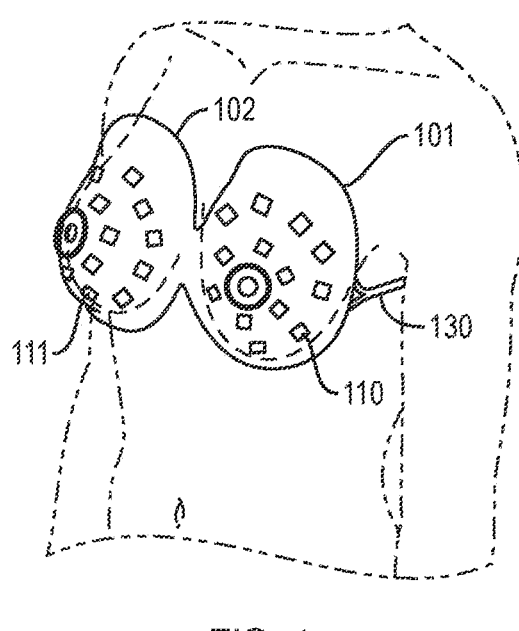
FIG. 1 shows two ultrasound patches that conform to curvilinear surfaces of a human body.
FIG. 2 shows a wearable control module.

FIG. 1 shows two conformable ultrasound patches, in an illustrative implementation of this invention. In FIG. 1, two ultrasound patches 101 and 102 conform to the outer surface of the left and right breasts, respectively, of a woman. Patch 101 fits snugly against the skin, throughout a curved region that covers almost all of the external surface of the left breast. Likewise, patch 102 fits snugly against the skin, throughout a curved region that covers almost all of the external surface of the right breast.

In FIG. 1, patches 101 and 102 each adhere or stick to the woman's skin due to Van der Waals attractive forces, without any gel or tape, and without requiring any external support structure to support the weight of the patches or to press the patches against the skin. Patches 101, 102 may be comfortably worn for long durations (e.g., hours or days). Patches 101, 102 may be easily removed from the skin, without damaging the skin, by pulling gently on them.

In some alternative implementations of this invention, one or more conformable patches are attached to a support structure, such as clothing (e.g., a bra). When a person wears the support structure (e.g., bra), the patch(s) may adhere or stick to the person's skin due to Van der Waals attractive forces. When the person stops wearing the support structure, the patches(s) may detach from the skin and remain attached to the support structure.

In FIG. 1, each conformable ultrasound patch 101, 102 comprises: (a) a flexible, elastomeric substrate and (b) phased arrays of rigid piezoelectric ultrasound transducers, which are embedded in the substrate. For instance, multiple phased arrays (including phased array 110) are housed in patch 101. Likewise, multiple phased arrays (including phased array 111) are housed in patch 102.

In FIG. 1, a link 130 delivers power to patches 101, 102. The patches may also communicate with a control module 140 via link 130. For instance, control module 140 may, via link 130, send instructions that control the timing of ultrasound pulses emitted by transducers in the phased arrays. Likewise, patches 101, 102 may take ultrasound measurements and send data that encodes the measurement to control module 140 via link 130. Link 130 may include: (a) one or more wires for delivering power; and (b) one or more wires or fiber optic links that are dedicated to communication.

FIG. 2 shows a wearable control module, in an illustrative implementation of this invention. In FIG. 2, control module 140 is supported by link 130 and is wearable. Control module 140 may control the phased arrays in patches 101 and 102. Among other things, control module 140 may separately control each ultrasound transducer in a given phased array, causing the transducers in the array to pulse in a temporal sequence in such a way as to steer (control the angle of) an ultrasound beam emitted by the phased array. Also, control module 140 may receive data that represents measurements taken by patches 101, 102, and may transmit this data to one or more other computers. In some cases, control module 140 wirelessly transmits the data. In some cases, control module 140 performs signal processing or otherwise processes the data, before transmitting it.

In FIG. 2, control module 140 provides power to the phased arrays in an ultrasound patch. In some cases, the power consumption of control module 140 and an entire ultrasound patch (including phased arrays) that it controls is less than 500 mW.

Figure 3:
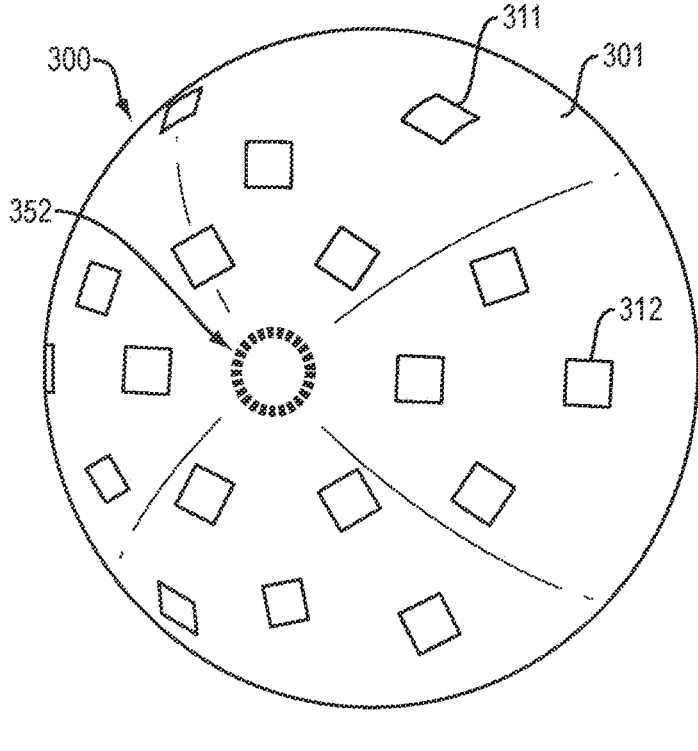
FIG. 3 shows an ultrasound patch.

FIG. 3 shows an ultrasound patch, in an illustrative implementation of this invention. In FIG. 3, patch 300 comprises (a) a flexible, elastomeric substrate 301; (b) phased arrays of rigid piezoelectric ultrasound transducers, which are embedded in the substrate; and (c) a ring 352 of ultrasound transducers that are also embedded in the substrate.

In FIG. 3, substrate 301 of a patch is configured to fit around, and to conform to, the external surface of a woman's breast. Substrate 301 may be sized and shaped in such a way that it has a concave inner surface that conforms to, and fits snugly against, a convex external surface of a woman's breast. Put differently, substrate 301 may be sized and shaped in such a way that it would, without any stretching, conform snugly to the external surface of a woman's breast if the breast happened to have a particular shape and size that matches that of the patch. However, the shape and size of breasts varies in a population of women. To accommodate the different shapes and sizes, substrate 301 may be flexible. Thus, substrate 301 may elastically stretch or deform in such a way as to fit snugly over a breast of the woman.

This invention is not limited to ultrasound imaging of breasts. In some alternative implementations, substrate 301 is shaped and sized in such a way that it conforms to, and fits snugly against, any curvilinear body part, such as a shoulder, wrist, toe, finger, toe joint or finger joint. In these alternative implementations, patch 300 may take ultrasound measurements that are used to generate a 3D image of a volume of the curvilinear body part.

In FIG. 3, phased arrays of piezoelectric ultrasound transducers are encapsulated in patch 300. The phased arrays (e.g., 311 and 312): (a) may emit ultrasound beams and steer them throughout a volume of tissue; and (b) and may also measure ultrasound echoes that reflect from tissue.

In FIG. 3, a ring 352 of piezoelectric ultrasound transducers is employed for localization, to determine the 3D position of each of the phased arrays in patch 300.

In a protype of this invention: (a) the ultrasound patch is less than 2 mm thick; (b) the ultrasound patch has a diameter of 10 cm, when the patch is not stretched to conform to a surface of a body part; (c) the dimensions of each phased array in the patch are 6 mm×6 mm×1 mm; (d) a 1 cm diameter hole in the center of the patch is configured to encircle a breast nipple placement; (e) a ring array in the center of the patch (around the nipple) is employed to determine the 3D position of each phased array in the patch; and (f) the distance between each pair of neighboring phased arrays is 2 cm, when the patch is not stretched to conform to a surface of a body part.

The prototype described in the preceding paragraph is a non-limiting example of a patch. The dimensions of a patch and of the components of the patch may be different, in other implementations of this invention. The spatial distribution of phased arrays (e.g., 311, 312) in the soft substrate of the patch may depend on the beam steering angle in two directions (elevation and azimuth) of each of the phased arrays.

Beam Steering

In illustrative implementations, each phased array in a patch performs beam steering. In this beam steering, each phased array emits an ultrasound beam, while varying the orientation of the beam relative to the phased array. For instance, the angle of the beam, relative to the phased array, may vary over a wide range of angles (e.g., over more than 100 degrees). As the orientation of the beam changes, the beam may sweep through a volume of tissue.

In illustrative implementations, beam steering enables each phased array in a patch to measure ultrasound echoes from a large volume. This in turn may reduce the number of phase arrays that are needed in the patch, and may eliminate (or reduce) gaps in the ultrasound image that is captured by the patch.

Figure 4:
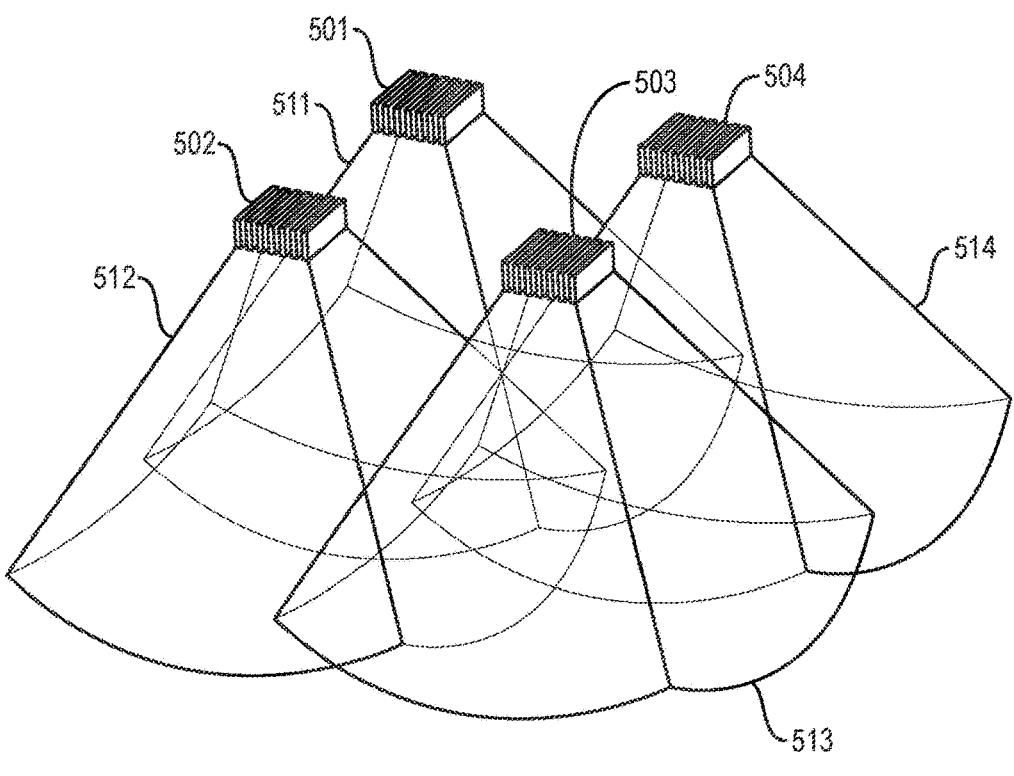
FIGS. 4 and 5 illustrate beam steering.
Figure 5:
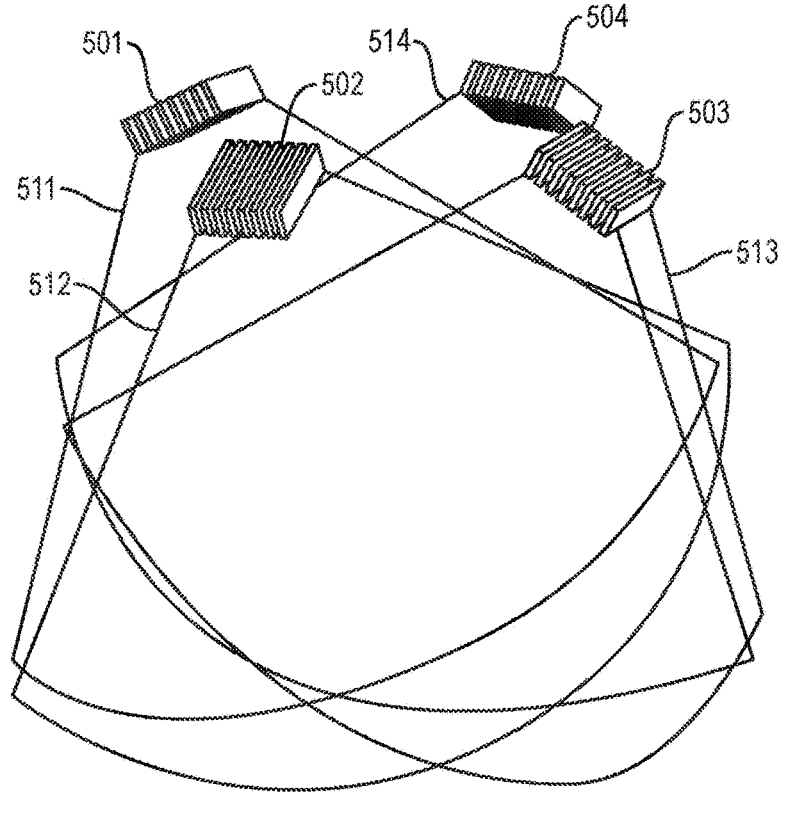

FIGS. 4 and 5 illustrate beam steering. In FIGS. 4 and 5, four phased arrays 501, 502, 503, 504 each emit an ultrasound beam and perform beam steering. During the beam steering, phased array 501 emits an ultrasound beam and steers the beam in such a way that the beam: (a) sweeps through an entire volume 511; and (b) occupies different parts of volume 511 at different times. Likewise, during the beam steering, phased array 502 emits an ultrasound beam and steers the beam in such a way that the beam: (a) sweeps through an entire volume 512; and (b) occupies different parts of volume 512 at different times. Similarly, during the beam steering, phased array 503 emits an ultrasound beam and steers the beam in such a way that the beam: (a) sweeps through an entire volume 513; and (b) occupies different parts of volume 513 at different times. Likewise, during the beam steering, phased array 504 emits an ultrasound beam and steers the beam in such a way that the beam: (a) sweeps through an entire volume 514; and (b) occupies different parts of volume 514 at different times.

In FIG. 4, phased arrays 501, 502, 503, 504 are in a planar configuration. Specifically, in FIG. 4, the phased arrays are spatially arranged in such a way that they fit snugly against a single geometric plane.

In FIG. 4, phased arrays 501, 502, 503, 504 are arranged in a non-planar configuration. Specifically, in FIG. 5 the phased arrays are spatially arranged in such a way that they fit snugly against a curved surface.

The volumes that are imaged by phased arrays 501, 502, 503, 504 are different in FIGS. 4 and 5, due to the different positions of the phased arrays.

The beam steering may be performed as follows. In a given phased array, each row or column of transducers in the phased array may be pulsed individually, in such a way that different rows or columns of transducers in the array emit an ultrasound pulse at different times. For instance, in some cases, the transducers in an array are pulsed sequentially, one row or column of transducers at a time. The ultrasound wavefront emitted by an individual row or column of ultrasound transducers may be spherical. However, the wavefronts emitted by all of the transducers in a patch may combine to form a quasi-planar wavefront. Specifically, the wavefronts emitted by the individual transducers in the phase arrays may combine by superposition (i.e., constructive and destructive interference) to form the quasi-planar wavefront.

In illustrative implementations, the direction (relative to the phased array) in which the quasi-planar wavefront travels is determined by phase differences between the individual wavefronts, which in turn is due to time delays between pulses (i.e., differences in the time at which the different transducers are pulsed). Thus, by controlling the timing of the ultrasound pulses emitted by transducers in a phased array, the phased array may control the direction in which an ultrasound beam (which is emitted by the phased array) travels.

In some cases, an electronic oscillator in control module 140 outputs a periodic electrical signal. This signal in turn may be employed to generate a set of electrical signals, each with a different time delay (phase offset). This set of electrical signals may in turn drive the ultrasound transducers in the phased array, in such a way that different transducers in the array are pulsed with different time delays.

In some implementations, each piezoelectric ultrasound transducer in a phased array is pulsed independently. Varying the timing (at which different transducers are pulsed) causes the phased array to radiate a quasi-plane ultrasonic beam at an angle relative to the phased array. The beam may be steered electronically and dynamically by changing the time delays and thus the angle at which the beam is radiated.

In some implementations, each phased array emits a quasi-planar ultrasound beam that sweeps through a volume shaped like a truncated pyramid. In some cases, the maximum beam steering angle (at −6 dB) may be calculated by $\sin \theta_{st}=0.514\cdot\lambda/w$, where $\theta_{st}$ is the maximum steering angle, $\lambda$, is the wavelength in the medium, and w is the element width, respectively. Based on this equation, the angle may be larger than 30° when the width is equal to or less than the wavelength (around 200 µm for 7.5 MHz).

In some implementations, each phased array emits an ultrasound beam and steers the beam, in such a way that the orientation of the beam relative to the array varies through a range of angles (relative to the array), where the angular difference between one end of the range and the other end of the range is at least 10 degrees, or at least 20 degrees, or at least 30 degrees, or at least 40 degrees, or at least 50 degrees, or at least 60 degrees, or at least 70 degrees, or at least 80 degrees, or at least 90 degrees, or at least 100 degrees, or at least 110 degrees, or at least 120 degrees, or at least 130 degrees, or at least 140 degrees, or at least 150 degrees.

To avoid echo interference between phased arrays, the phased arrays in a patch (or in a set of patches) may transmit in a temporal sequence, one phased array at a time.

Localization

In illustrative implementations, a conformable ultrasound patch detects the relative 3D positions of phased arrays in the patch. This is desirable, because the relative 3D positions of the phased arrays in the patch may otherwise be unknown, since these 3D positions may change as the patch conforms to the external surface of a curved body part. For instance, the distance between phased arrays of a patch may vary as the patch bends and stretches to conform to a curved body part.

In illustrative implementations, it is helpful to know the 3D positions of the phased arrays, when computing an ultrasound image of a region that includes overlapping volumes of tissue that are measured by the phased arrays.

In illustrative implementations, each ultrasound patch includes both: (a) an array of ultrasound transducers that is dedicated to localization ("localization array") and (b) multiple phased arrays. The localization array in a patch may transmit ultrasound pulses. The amount of time that it takes for these pulses to reach a phased array may be measured, and used to calculate the 3D position (relative to the localization array) of each of the phased arrays in the patch.

In some cases, the transducers in the localization array are piezoelectric ultrasound transducers. In some cases, each ultrasound transducer in a localization array has the same structure, the same dimensions, and is composed of the same materials as an ultrasound transducer in a phased array.

In illustrative implementations: (a) the localization array is a rigid structure; and (b) the ultrasound transducers in the localization array are in a fixed, constant position relative to each other.

In some cases, the localization array comprises a set of ultrasound transducers that are arranged in an annular pattern (ring). In some implementations: (a) an ultrasound patch conforms to a woman's breast; (b) the localization array of the patch is a ring-like structure that encircles the nipple of the breast; and (c) the nipple of the breast protrudes through a hole in the center of the localization array. However, the localization array may be implemented in many different ways. For instance, in some cases, the localization array has a shape that is not circular. In alternate implementations, the transducers in a localization array may be arranged in any constant spatial configuration relative to each other. In some cases, the localization array does not have a hole in its center, for a body part to fit through.

In some cases, localization is performed by measuring the amount of time (time-of-flight) that it takes for an ultrasound pulse to travel from a transducer in the localization array to a transducer in a phased array. In some cases, the ultrasound pulses (for localization) travel in the substrate of the patch when propagating from the localization array to a phased array. The substrate (through which the localization pulses travel) may comprise a sheet or layer of an Ecoflex® elastomer.

Figure 6:
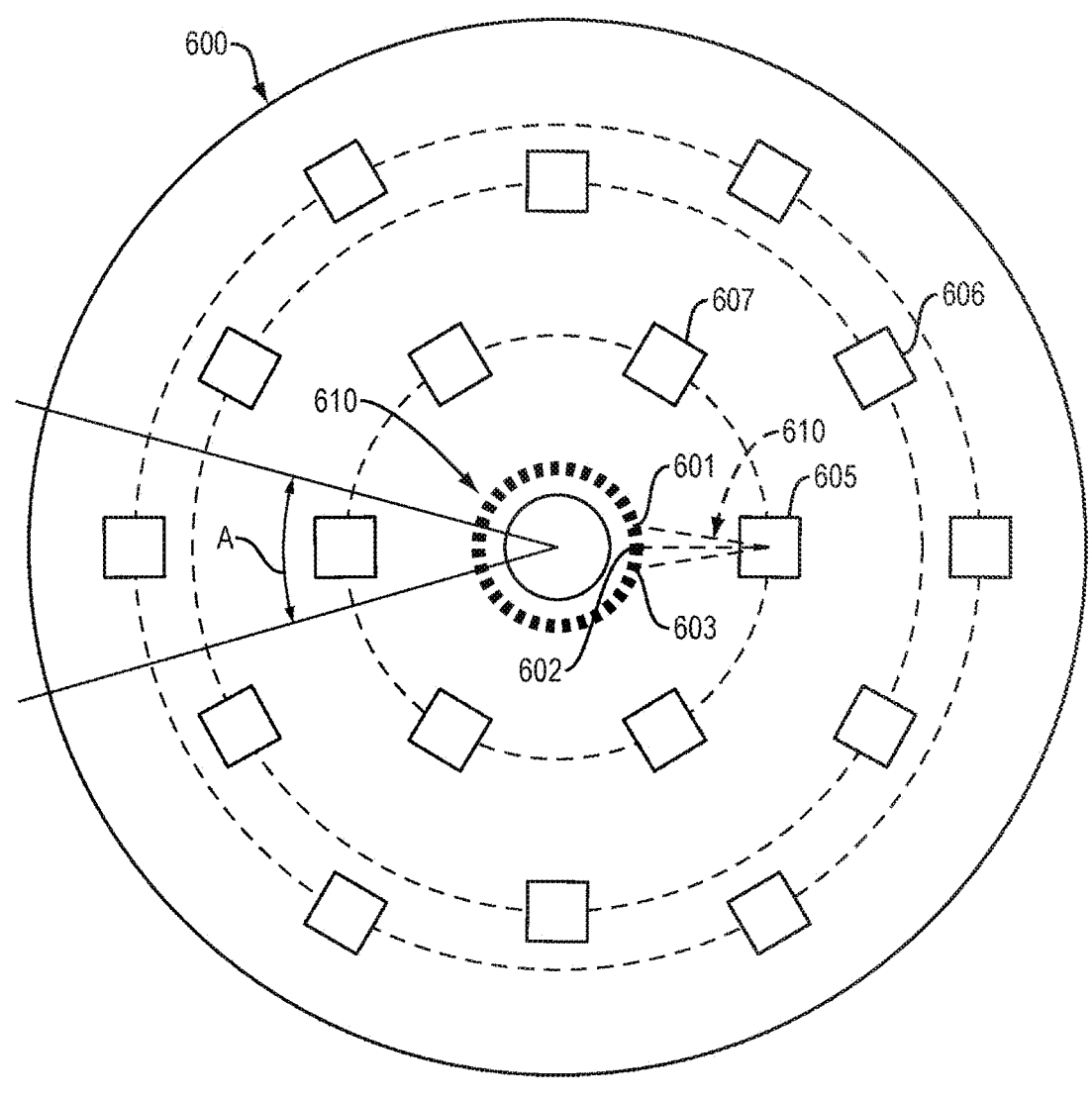
FIG. 6 illustrates hardware that is used for localization.

FIG. 6 illustrates hardware that is employed for localization, in an illustrative implementation of this invention. FIG. 6 is a top view of a conformable ultrasound patch 600. In FIG. 6, a set of phased arrays (e.g., 605, 606, 607) are encapsulated in patch 600. A rigid, annular array 610 (ring array) of piezoelectric ultrasound transducers is also encapsulated in patch 600. The center of the circle formed by ring array 610 is located at the radial center of patch 600.

In FIG. 6, ring array 610 is employed to detect the 3D position of each of the phased arrays in patch 600. For instance, to detect the 3D spatial position of phased array 605, three transducers 601, 602, 603 of ring array 610 emit ultrasound pulses. The pulses may travel in all directions, including along one-way paths 610 to phased array 605. The "time-of-flight" (amount of time that it takes for the pulse to reach phased array 605) is measured for each of these pulses. Based on these times-of-flight, the distances between transducers 601, 602, 603 and phased array 605 are calculated. Then the 3D position of phased array 605 is calculated as being at the intersection of three spheres that are centered on the three transducers in the ring array, as described above.

In FIG. 6, the three transducers (in the ring array) that emit the localization pulses may (when the patch is viewed from above) be located in a fan-shaped area. The fan-shaped region may include the phased array whose position is being detected and the three transducers that emit pulses to detect this position. The fan-shaped region may spread out from the center of a circle formed by the ring array. This fan-shaped region may extend over an angle A (e.g., 30 degrees) when seen from this center.

In some cases, at least three transducers in the localization each emit an ultrasound pulse, one transducer at a time. A phased array in the patch measures how long it takes for the pulses to reach the phased array.

Consider the following example (Example 1). In Example 1, the localization array comprises a rigid array (a ring array) of ultrasound transducers that are arranged in a circle. In Example 1, the ring array comprises 24 ultrasound transducers. Let us call the n phased arrays in the patch P1, P2, P3, . . . , Pn. Let us call the 24 ultrasound transducers in the ring array E1, E2, E3, . . . , E24.

In Example 1, the 3D spatial position of phased array P1 relative to the ring array is detected. To do so, three transducers (E1, E2, E3) in the ring array emit ultrasound pulses at different times and how long it takes for each of the three pulses to reach phased array P1 may be measured. Specifically, transducer E1 in the ring array transmits an ultrasound pulse which is received by phased array P1. Based on the amount of time that it takes for this one-way trip (from E1 to P1) and based on the known speed of ultrasound propagation in an elastomeric layer of the patch, the distance D1 between E1 and P1 is calculated. Then transducer E2 in the ring array transmits an ultrasound pulse which is received by phased array P1. Based on the amount of time that it takes for this one-way trip (from E2 to P1) and based on the known speed of ultrasound propagation in an elastomeric layer of the patch, the distance D2 between E2 and P1 is calculated. Then transducer E3 in the ring array transmits an ultrasound pulse which is received by phased array P1. Based on the amount of time that it takes for this one-way trip (from E3 to P1) and based on the known speed of ultrasound propagation in an elastomeric layer of the patch, the distance D3 between E3 and P1 is calculated. The 3D position of phased array P1 is calculated as being at the intersection of a first sphere, a second sphere and a third sphere, where the first sphere has a radius of D1 and is centered on E1, the second sphere has a radius of D2 and is centered on E2, and the third sphere has a radius of D3 and is centered on E3.

Likewise, in Example 1, the 3D location of phased array P2 may be detected by measuring how long it takes for pulses emitted by transducers E4, E5, E6 in the ring array to travel to phased array P2, in the same manner as described in the preceding paragraph.

In illustrative implementations, only a single transducer in a phased array (rather than all of the transducers in the phased array) takes measurements from which the time-of-flight of a localization pulse is calculated. For instance, a single ultrasound transducer at the center of a phased array (instead of all of the transducers in a phased array) may measure how long it takes for localization pulses to arrive.

In some cases, the positional data is resampled to compute the coordinates of the individual phased arrays, before the phased arrays capture ultrasound measurements for a new ultrasound image.

In some implementations, the closest three transducers in a ring array emit pulses that are used to detect the 3D position of a particular phased array. Specifically, these three transducers in a ring array may be closer to the particular phased array than are any other transducers in the ring array. In many cases, the bending and stretching that occurs when the patch conforms to a curved body part is unlikely to alter which three transducers in the ring array are closest to a particular phased array.

In some cases, the closest three transducers (when seen from a top view of the patch) are located in a fan-shaped area of the patch, which fan-shaped area includes the phased array whose 3D position is being measured. This fan-shaped area may spread out from the center of the circle formed by the ring array. For instance, the fan-shaped area may cover an angle of 30 degrees, as seen from this center.

In some cases: (a) the transducers in a center ring array are pulsed to generate an ultrasound wave in all directions; (b) only one phased array is switched on at a time, to measure ultrasound waves from at least three transducers in the ring array; (c) the three transducers are in a fan-shaped area (e.g., a great arc of 30 degrees) in which the phased array is also located; (c) the phased arrays are localized one by one and the 3D coordinates of each phased array is stored in a data processing system; (d) the phased arrays each separately take measurements for a 3-D image of a local area by phased array beam steering; (d) a computer reconstructs an image of an entire tissue region (e.g., breast) by combining 3-D images; and (e) the 3D coordinates of the phased arrays are employed, when combining the images.

In some cases, only one phased array will be switched on, at any given time, to receive localization signals or to take ultrasound measurements to generate an image.

Figure 7C:
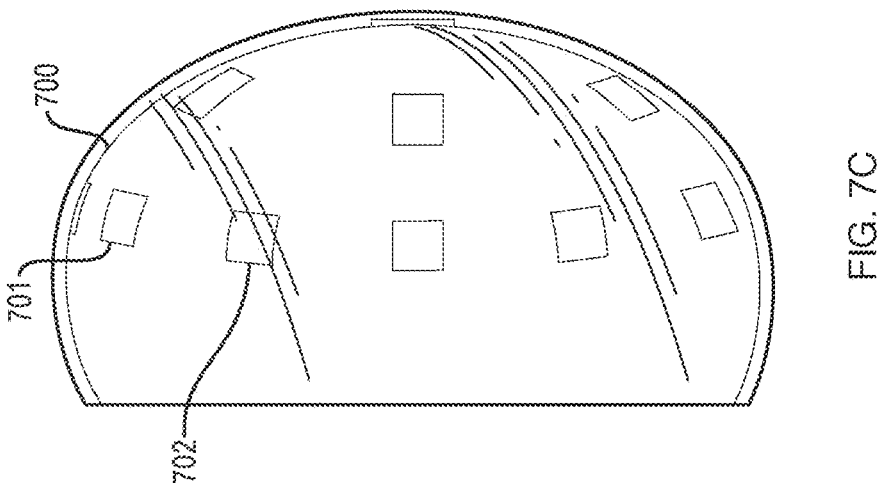
FIGS. 7A, 7B and 7C show different spatial configurations of an ultrasound patch as it conforms to different shapes of a curvilinear surface of a human body.
Figure 7B:
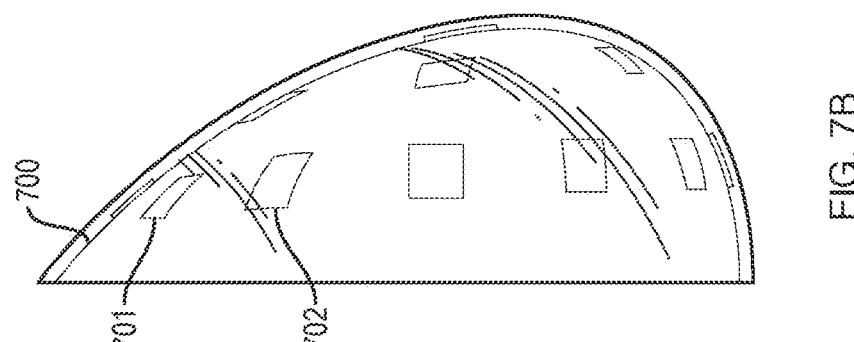
Figure 7A:
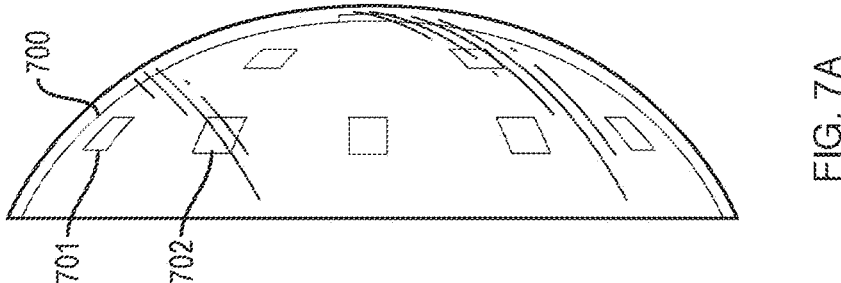

FIGS. 7A, 7B and 7C show different spatial configurations of an ultrasound patch as it conforms to different shapes of a curvilinear surface of a human body, in an illustrative implementation of this invention. Specifically, FIGS. 7A, 7B and 7C show different spatial configurations of an ultrasound patch 700 as it conforms to the external surface of a small breast, sagging breast and large breast, respectively, of different women. As patch 700 conforms to these different sizes and shapes of breasts, the relative positions of the phased arrays (e.g., 701, 702) in the patch change. This, in turn, may cause the volumes of tissue that are imaged by the phased arrays to change (similar to how the volumes of tissue imaged by phased arrays changes from FIG. 4 to FIG. 5). Thus, in illustrative implementations, it is desirable to perform localization to detect the 3D positions of the phased arrays.

Components of an Ultrasound Patch

In some implementations, two outer layers (e.g., top and bottom layers) of the ultrasound patch comprise a flexible, silicone elastomer or silicone rubber. The interior of the ultrasound patch may include: (a) a set of rigid phased arrays that are embedded in the patch; (b) a rigid localization array (e.g., a ring array) that is embedded in the patch and that is located in a central region of the patch; (c) what we call a "matching layer" (e.g., on top of each phased array); (d) what we call a "backing layer" (e.g., on the bottom of each phased array); and (e) electrodes and flexible electrical cables. Each phased array in the patch may comprise a rigid array of piezoelectric ultrasound transducers, with epoxy between the transducers.

Figure 8:
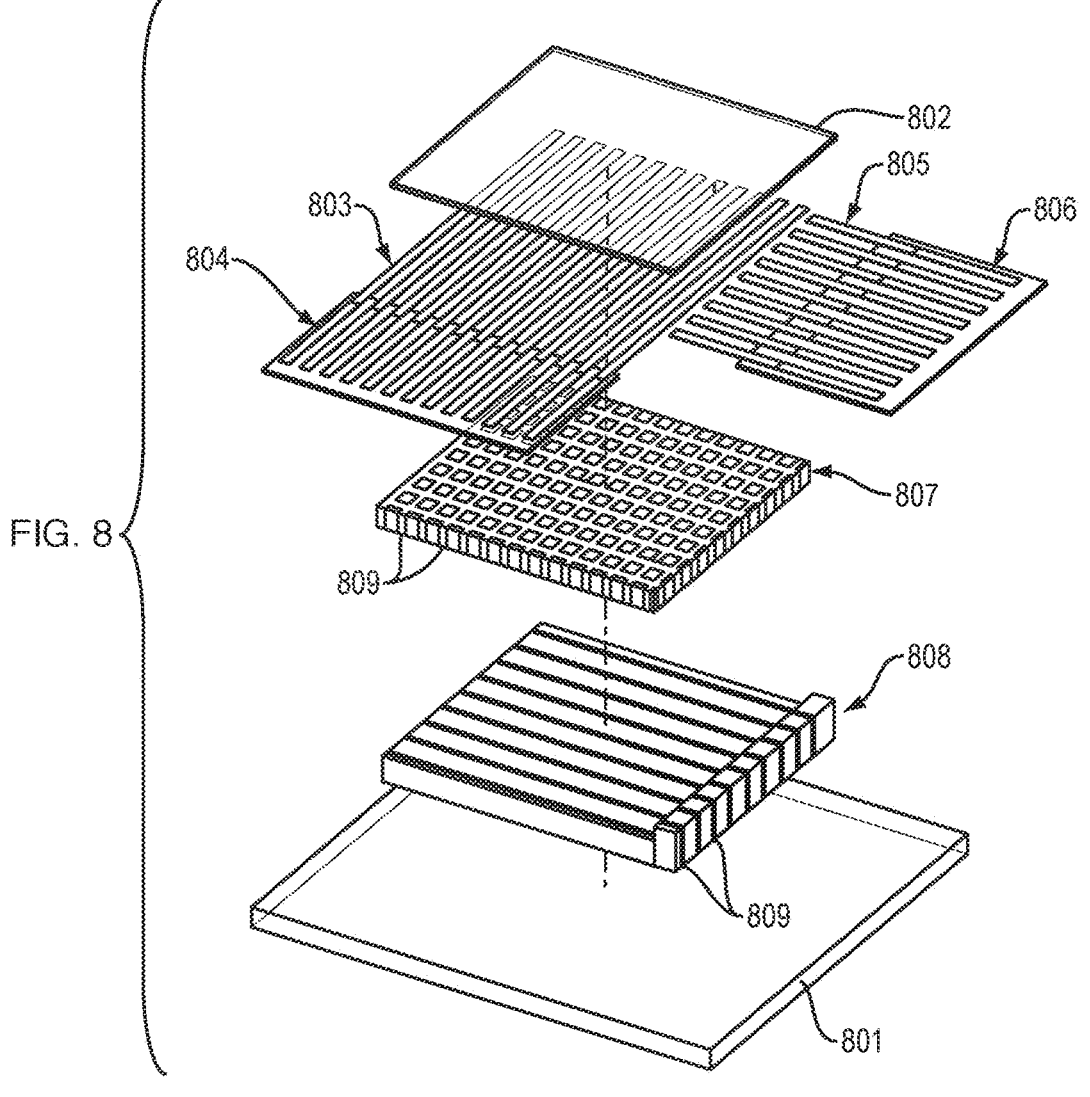
FIG. 8 is an exploded view of an ultrasound phased array.

FIG. 8 is an exploded view of a portion of an ultrasound patch, in an illustrative implementation of this invention. Specifically, FIG. 8 shows a portion of the patch that includes a single phased array. A "matching layer" 802 is located on one side (e.g., the top side) of the crystal array 807 of a phased array. Likewise, a "backing layer" 808 is located on an opposite side (e.g., the bottom side) of crystal array 807. A set of electrodes (803, 805) and flexible electrical cables (804, 806) are electrically connected to piezoelectric ultrasound transducers in the phased array. Each phased array in the patch may comprise an array of crystals 807, where each of the crystals is a piezoelectric ultrasound transducer. Epoxy 809 may fill spaces between the individual transducers in crystal array 807 and may fill spaces between different portions of backing layer 808.

For clarity and simplicity of illustration, in FIGS. 8, 9, 10, 11, and 12, phased arrays are shown with a relatively small number of elements (ultrasound transducers). For instance: (a) in FIG. 8, crystal array 807 is shown as a 13×10 array of ultrasound transducers; (b) in FIGS. 9, 10 and 11, the phased array is shown as a 3×3 array of ultrasound transducers; and (c) in FIG. 12, phased array 1200 is shown as an 8×8 array. In actual practice, the number of transducers in the array may be much larger. For instance, in some cases, each phased array is a 16×16, or 32×32, or 64×64, or 128×128 array of ultrasound transducers.

In illustrative implementations, each phased array is a rigid structure.

In FIG. 8, a phased array is surrounded (on its sides and bottom, but not on the top) by an intermediate layer 801. Intermediate layer 801 may be positioned between a rigid phased array and a flexible substrate, and may reduce stress and strain that would otherwise occur at an interface between the rigid array and the flexible substrate. For instance, stress and strain may be distributed from a surface of a phased array to intermediate layer 801, and then to the flexible substrate. FIG. 8 shows a portion, but not all, of intermediate layer 801. In some cases, intermediate layer 801 does not cover the top side of the phased array, and thus does not cover the matching layer (which is on the top side of the phased array). In some cases, power and communication links (e.g., electrodes and cables) pass through the intermediate layer 801.

In some cases, matching layer 802 prevents interstices reflections, and also enhances acoustic transmission. The matching layer 802 may be prepared by spin-coating on the upper surface of a phased array. In some cases, matching layer 802 is electrically insulative. For instance, the matching layer may comprise epoxy with inorganic micro-sized fillers (e.g., $BaTiO_3$, $Al_2O_3$, Ag). The thickness of the matching layer may be equal to one quarter of the wavelength of an ultrasound wave in this matching layer.

The matching layer 802 and backing layer 808 may have an intermediate acoustic impedance that is between acoustic impedance of the hard piezoelectric transducers and the acoustic impedance of the soft biological tissue being imaged. The matching and backing layers may be attached to front- and back-sides, respectively (or the top and bottom sides, respectively) of the piezoelectric ultrasound transducers in a phased array.

In some cases, backing layer 808 is conductive. For instance, backing layer 808 may comprise a conductive epoxy mixture (E-SOLDER®3022), which has a good acoustic performance. In some cases, the backing layer for a single piezoelectric transducer crystal is fabricated by centrifuging and lapping a conductive epoxy mixture (e.g., E-SOLDER® 3022) uniformly onto the crystal.

In some cases, a transparent epoxy (e.g., 809) fills spaces between the transducers in a phased array. For instance, the transparent epoxy may comprise EPO-TEK®301. The transparent epoxy 809 may fill the kerf and eliminate the transverse vibration of the single transducer crystals.

In some cases, the electrodes (e.g., 803, 805) comprise one or more of the following elements or an alloy of one or more of the following elements: silver (Ag), aluminum (Al); gold (Au); cobalt (Co); chromium (Cr); copper (Cu); iron (Fe); molybdenum (Mo); niobium (Nb); nickel (Ni); tungsten (W); and zinc (Zn). For instance, in some cases, the electrodes comprise: (a) Au/Ti (an alloy of gold and titanium); (b) Cr/Au (an alloy of chromium and gold); (c) Pt/Cr (an alloy of platinum and chromium); or (d) Ti/Pt (an alloy of titanium and platinum). In some cases, the electrodes comprise epoxy-based conductors (e.g., silver epoxy), indium tin oxide (ITO) or any combination thereof.

In some cases, signal crosstalk between adjacent microfabricated interconnection electrodes is reduced or eliminated by one or more of the following strategies: permanent metal shielding, sufficient gap distance between power and signal lines, and engineering the frequencies of the transmitted and received signals.

In some cases, flexible cables connect each of the phased arrays in the patch to an external power and data processing device. To achieve this, electrodes may be aligned and bonded with heat seal connectors or other polyimide-based flexible cables.

In some cases, each of the rigid phased arrays in a patch is bonded on Ecoflex® by UV (ultraviolet) ozone and hot-pressing.

Phased Array

Figures 9, 10:
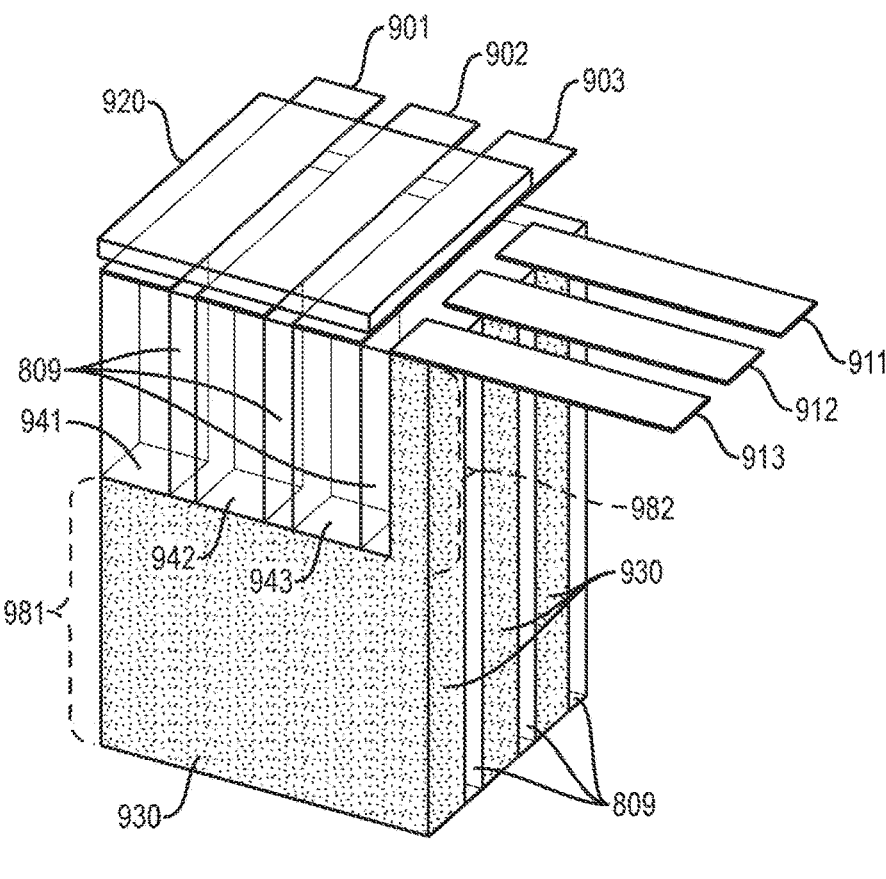
FIGS. 9, 10 and 11 are zoomed-in views of an ultrasound phased array.
Figure 11:
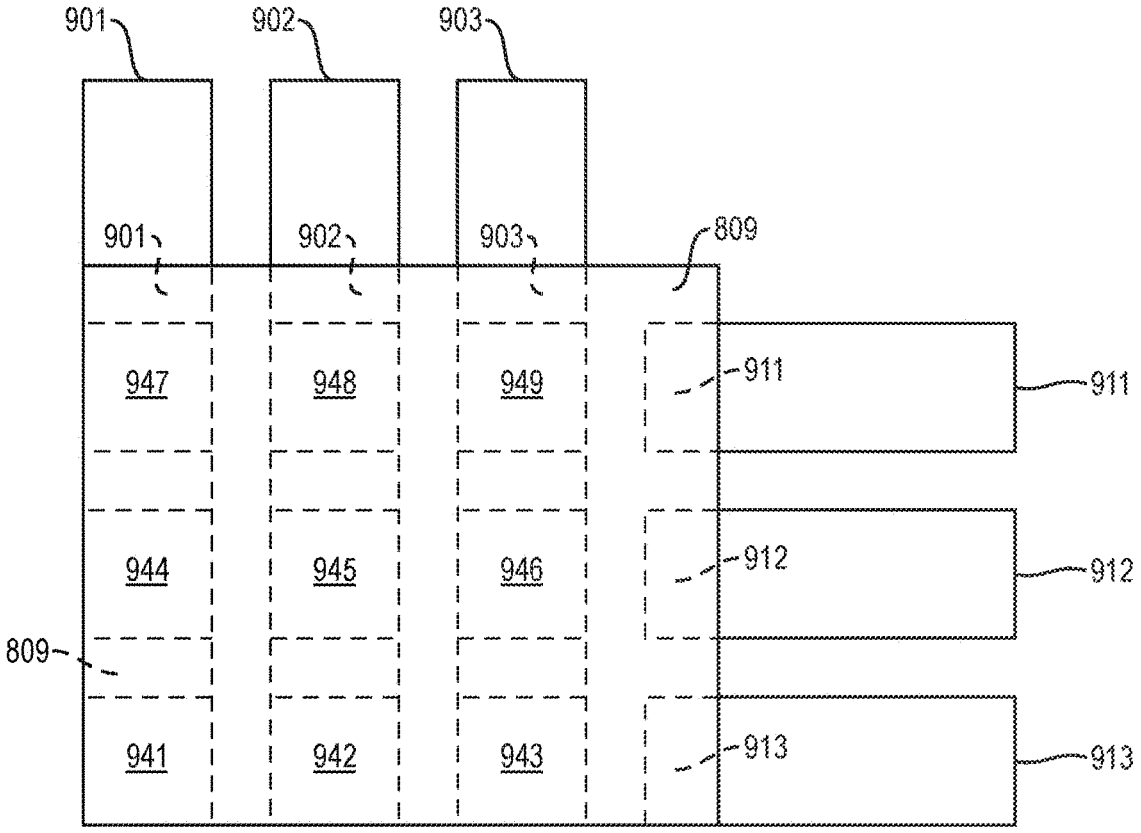

FIGS. 9, 10 and 11 show a phased array, in an illustrative implementation of this invention. FIG. 9 shows a perspective view of the phased array. FIG. 10 shows a central portion of the same phased array, without "backing" and "matching" layers. FIG. 11 shows a top view of the same array.

As shown in FIG. 10, a central portion of the phased array comprises nine piezoelectric ultrasound transducers 941, 942, 943, 944, 945, 946, 947, 948, 949. An electrically insulative epoxy 809 fills spaces between the transducers and between different portions of a "backing" layer 930.

In FIGS. 9, 10, and 11, the phased array includes: (a) piezoelectric ultrasound transducers 941, 942, 943, 944, 945, 946, 947, 948, 949; (b) a "backing" layer 930; (c) a "matching" layer 920; (d) electrodes 901, 902, 903, 911, 912, 913 that connect to the transducers; and (e) epoxy that fills spaces between transducers.

As shown in FIG. 9, backing layer 930 not only covers the bottom surface of the piezoelectric transducers, but also attaches to electrodes 911, 912, 913. The backing layer 930 may comprise E-SOLDER®3022. The backing layer 930 may be electrically conductive, and may function as the bottom electrode for each of the ultrasound transducers in the phased array. The backing layer 930 may be separated into multiple parts, and epoxy 809 may fill the spaces between the different parts of the backing layer 930.

As shown in FIG. 9, the bottom side of the transducers may be electrically connected, via the conductive backing layer 930, to electrodes 911, 912, 913. Also, the top side of the transducers may be electrically connected to electrodes 901, 902, 903.

Thus, as shown in FIG. 9, electrical connections to both the bottom and top sides of the ultrasound transducers are achieved, even though the electrodes 901, 902, 903, 911, 912, 913 all connect to the phased array at the same vertical level (at the top side of the transducers). This approach (in which all of the electrodes for a phased array connect to the phased array at the same vertical level) may simplify fabrication of the phased array.

A first portion 981 of the backing layer 930 may be attached to (and may physically touch) the bottom of the transducers. A second portion 982 of the backing layer 930 may extend up a side of the phased array to reach electrodes 911, 912, 913. In FIG. 9, this second portion 982 of backing layer 930: (a) does not touch the piezoelectric transducers, and (b) instead touches an electrically insulative epoxy 809 that fills spaces between this second portion and the transducers. The first (bottom) portion 981 of backing layer 930 may be divided into separate sections that are separated from each other by the electrically insulative epoxy 809 and that correspond to rows of the array. Likewise, the second (side) portion 982 of backing layer 930 may be divided into separate sections that are separated from each other by the electrically insulative epoxy 809 and that correspond to rows of the array.

In some cases, a phased array is fabricated as follows: First, a single piezoelectric crystal with backing layer is diced completely in one direction (row) and filled with electrically insulative epoxy (e.g., EPO-TEK®301). Second, the single crystal (but not the backing layer) is diced in the other direction (column). This leaves the backing layer still connected to the transducers in one direction (row). The epoxy fills spaces between the transducers in the array. The matching layer is spin coated on the top side of the transducers in the array. This paragraph describes a non-limiting example of this invention. This invention may be implemented in many other ways.

In some cases, the pitch between transducers is 100 μm and the width of each transducer depends on the thickness of blade (e.g., 70 μm in width and 30 μm in kerf). In some cases, the pitch is equal to a half wavelength (0.5λ) at the transducer's working frequency. This pitch may balance two design goals: (a) easy microfabrication; and (b) avoiding side lobes by keeping the pitch less than 0.6λ. For instance, the pitch of the array may be equal to half of wavelength and may change from 360 μm to 50 depending on the working frequency of the transducers.

In illustrative implementations of this invention, transducers in a phased array transmit and receive ultrasound. For instance, in some cases, rows of ultrasound transducers in a phased array transmit ultrasound, one row at a time, while columns of ultrasound transducers in the array receive ultrasound reflections. In other cases, columns of ultrasound transducers of a phased-array transmit ultrasound, one column at a time, while rows of ultrasound transducers in the array receive ultrasound reflections.

Figure 12:
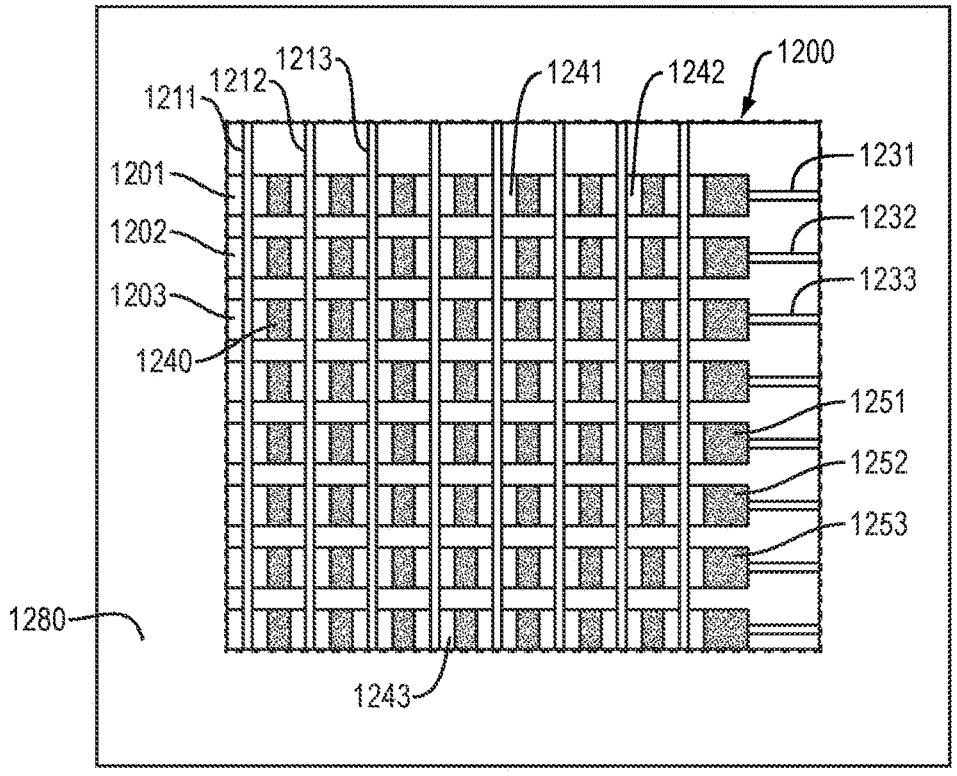
FIG. 12 shows a top view of an ultrasound phased array.

FIG. 12 shows a top view of another ultrasound phased array. In FIG. 12, a phased array 1200 comprises an 8×8 array of piezoelectric ultrasound transducers (e.g., 1201, 1202, 1203, 1241, 1242, 1243). The phased array is connected to column electrodes (e.g., 1211, 1212, 1213) and to row electrodes (e.g., 1231, 1232, 1233). Both the column electrodes and the row electrodes are electrically connected to the phased array at the same vertical level, which is immediately above the top side of the piezoelectric ultrasound transducers. The top side of the transducers is shown in FIG. 12 and is in direct physical contact with the column electrodes. The bottom side of the transducers is not shown in FIG. 12 and is in direct physical contact with the conductive "backing" layer. The "backing" layer appears stippled in FIG. 12. In FIG. 12: (a) the right-hand column of stippled rectangles (including rectangles 1251, 1252, 1253) shows a portion of the backing layer that extends up a side of the phase array and connects with row electrodes (e.g., 1231, 1232, 1233); and (b) the other stippled rectangles (e.g., 1240) are portions of the backing layer that underneath the transducers. In FIG. 12, the phased array is shown without the epoxy that fills the spaces between the transducers. In FIG. 12, an intermediate layer 1280 surrounds all four sides and the bottom of the phased array.

Ultrasound Transducer

In some implementations, each individual ultrasound transducer in a phased array comprises a single piezoelectric crystal of $Pb(Mg_{1/3}Nb_{2/3})O_3$—$PbTiO_3$ (PMN-PT).

In other cases. each individual ultrasound transducer in a phased array comprises a piezoelectric material $Pb(Zr, Ti)O_3$ (PZT).

In yet other cases, each piezoelectric ultrasound transducer in a phased array comprises one or more of the following materials: berlinite ($AlPO_4$), quartz, rochelle salt, topaz, tourmaline-group minerals, gallium orthophosphate ($GaPO_4$), langasite ($La_3Ga_5SiOi_4$), barium titanate ($BaTiO_3$), lead titanate ($PbTiO_3$), lead zirconate titanate ($Pb[Zr_xTi1-x]O_3$, $0<x<1$) (commonly referred to as PZT), lead magnesium niobate (PMN), lead magnesium niobate-lead titanate (PMN-PT), $Pb(In_{1/2}Nb_{1/2})O_3$—$Pb(Mg_{1/3}Nb_{2/3})O_3$—$PbTiO_3$ (PIN-PMN-PT), potassium niobate ($KNbO_3$), lithium niobate ($LiNbO_3$), lithium tantalate ($LiTaO_3$), sodium tungstate ($Na_2WO_3$), zinc oxide (ZnO), sodium potassium niobate (($K,Na)Nb_{O3}KNN$), bismuth ferrite ($BiFeO_3$), sodium niobate ($NaNbO_3$), bismuth titanate ($Bi_4Ti_3O_{12}$), Sodium bismuth titanate (NBT), polyvinylidene fluoride (PVDF), poly[(vinylidenefluoride-co-trifluoroethylene][P(VDF-TrFE)], or any combination thereof.

In some cases, the ultrasound transducers in the phased array all have the same working frequency. The working frequency may be in a range of 2 MHz to 15 MHz. The corresponding thickness of piezoelectric ultrasound transducers may be in a range from 1 mm to 0.12 mm (frequency constant divided by working frequency).

In some use scenarios: (a) the phased array is employed for ultrasound imaging of a woman's breast; (b) a working frequency of 5-12 MHz is recommended for the breast imaging; and (c) the working frequency of all of the ultrasound transducers in the patch is in the range of 5-12 MHz. For instance, in some cases, the working ultrasound frequency is 7.5 MHz. (The "working frequency" of an ultrasound transducer is the fundamental frequency of ultrasound that is transmitted by the transducer. It is not the frequency of the amplitude modulation—e.g., pulsing—of the ultrasound that is emitted.)

In illustrative implementations, each ultrasound transducer in a phased array is a piezoelectric crystal. The crystals in the array may both transmit and receive (detect) ultrasound. When voltage is applied to a piezoelectric crystal, the crystal may change size and shape, thereby causing the crystal to produce an ultrasound. When mechanical force is applied to a piezoelectric crystal, the crystal may generate a voltage. Thus, a piezoelectric crystal may detect and measure ultrasound that reflects from tissue. In some cases, each single piezoelectric crystal is employed for both transmitting and receiving ultrasound. In other cases, one or more piezoelectric crystals transmit ultrasound and one or more other piezoelectric crystals receive (detect and measure) ultrasound.

In some implementations, the transducers in the phased array perform two-way beamforming.

Control Module

Figure 13:
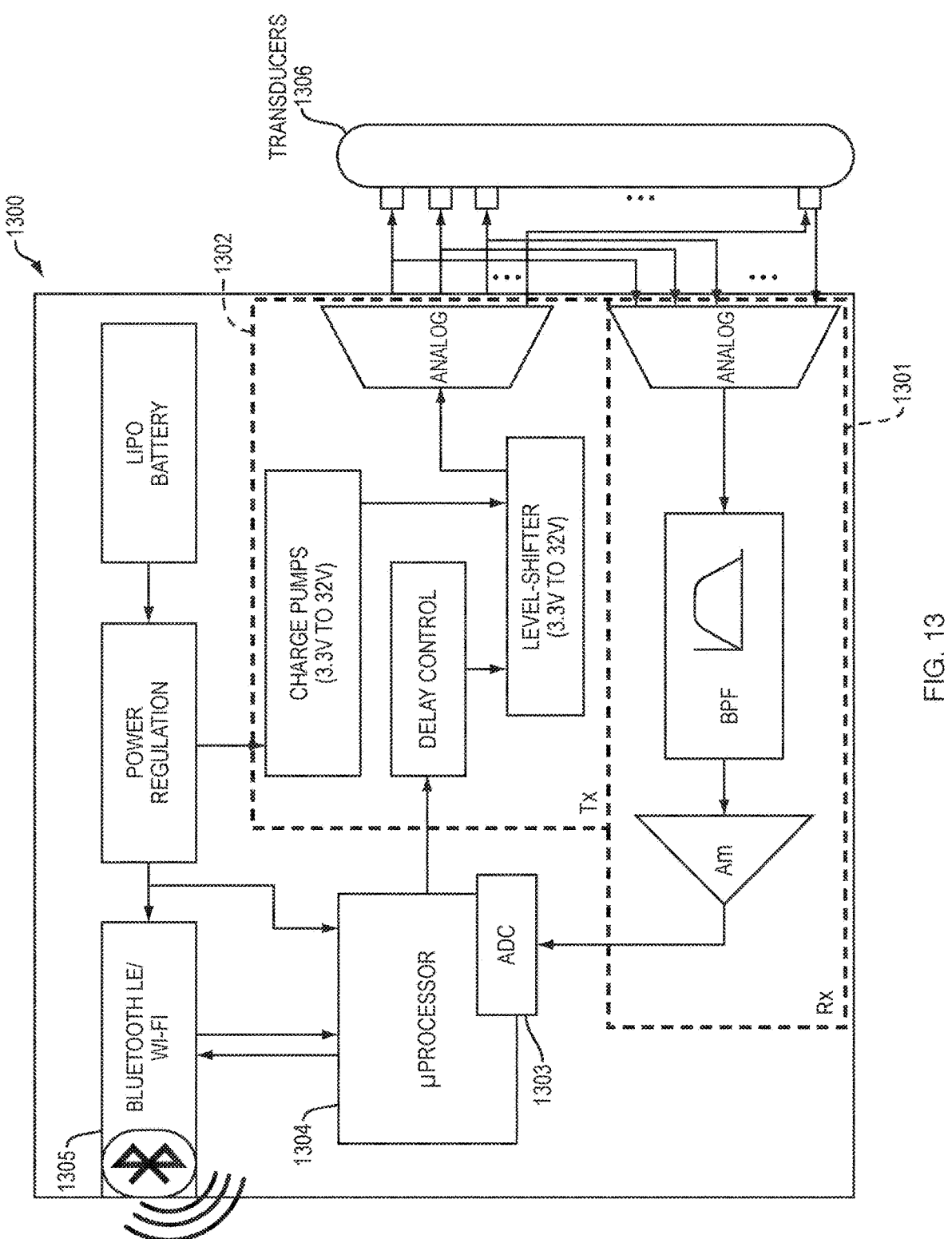
FIG. 13 is a schematic of a control module.

FIG. 13 is a schematic of a control module, in an illustrative implementation of this invention. In FIG. 13, a control module 1300 includes a receiver module 1301, a transmit module 1302, an ADC (analog-to-digital converter) 1303, a microprocessor 1304 and a wireless module 1305. The transmit module 1302 may generate analog electric signals that drive individual ultrasound transducers in the phased arrays. The receive module 1301 may process and amplify analog electric signals that encode measurements of ultrasound reflections which are measured by the ultrasound transducers of the patch. The ADC 1303 may convert an analog signal (i.e., the amplified analog output of the receiver module 1301) into a digital signal. The digital signal outputted by ADC 1303 may encode data regarding ultrasound measurements taken by transducers in the patch. The microprocessor 1304 may process this data and send the processed data to wireless module 1305. The wireless module 1305 may in turn transmit a wireless signal that encodes data regarding ultrasound measurements taken by the patch. The microprocessor 1304 may control, or interface with, receiver module 1301, transmit module 1302, ADC 1303, and wireless module 1305.

In some cases, control module 1300 includes an analog integrated circuit (IC). Control module 1300 may digitize ultrasound transducer readings, and send this data wirelessly to an external device for further processing, via a Bluetooth® wireless module. Control module 1300 may be powered by a lithium polymer battery, and may supply all of the peripherals through voltage regulation. The transmitter analog IC may include a charge pump component to provide a high actuation supply voltage, a delay control to enable ultrasound phase-array mode, and a level shifter to convert the digital output's low driving voltage to high actuation voltage. This tunable actuation voltage may then be directed sequentially to every ultrasound transducer in a phased array. A receiver component of the control module 1300 may multiplex the inputs and deploy a band-pass filter (BPF) to eliminate noise and reveal backscatter signals with the frequency of interest. These signals may then be amplified before being digitized by an internal analog-digital converter of control module 1300.

In some cases, control module 1300 includes a flexible printed circuit board and is connected to the ultrasound patch through conductive threads or flexible interconnects. The ultra-sound patch may be operator-independent, and may easily interface with a smart-phone app which captures scan data automatically.

Ultrasound Imaging System

Figure 14:
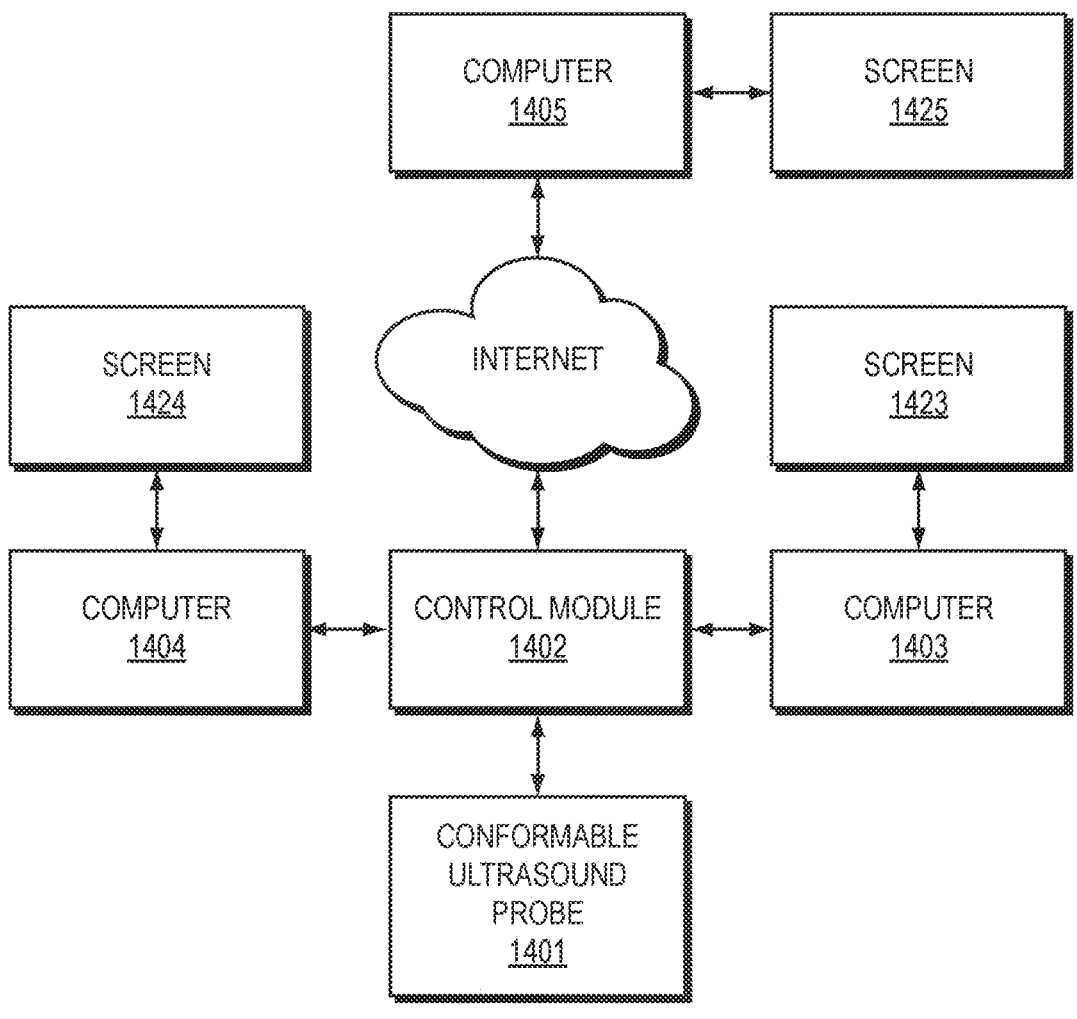
FIG. 14 shows hardware for an ultrasound imaging system.

FIG. 14 shows hardware for an ultrasound imaging system. In the example shown in FIG. 14, a conformable ultrasound patch 1401 takes measurements of ultrasound echoes from tissue. A control module 1402: (a) may provide power to patch 1401, (b) may control timing of pulses in phased arrays in patch 1401, may process data received from patch 1401, and may transmit data that encodes or is derived from the measurements taken by patch 1401. For instance, control module 1402 may transmit the data wirelessly to computer 1403. Or for instance, control module 1402 may send the data via a wired or fiber optic link to computer 1404. Computers 1403, 1404 and control module 1402 may be part of a LAN (local area network) or part of a WAN (wide area network). Alternatively, control module 1402 may send the data via the Internet to computer 1405. A computer (e.g., 1403, 1404 or 1405) may process the data and may cause an electronic display screen (e.g., 1423, 1424 or 1425) to display an ultrasound image.

Encapsulation of Phased Array

In illustrative implementations, each phased array is partially encapsulated by an intermediate layer. In some cases, the intermediate layer surrounds the bottom and four sides of a phased array, but does not cover the top of the phased array. In illustrative implementations, the intermediate layer is located between the phased array and the flexible substrate. The intermediate layer may help to distribute mechanical stress and strain that might otherwise occur in, and cause damage to, a region in which the rigid phased array is adjacent to the flexible substrate.

Figure 15:
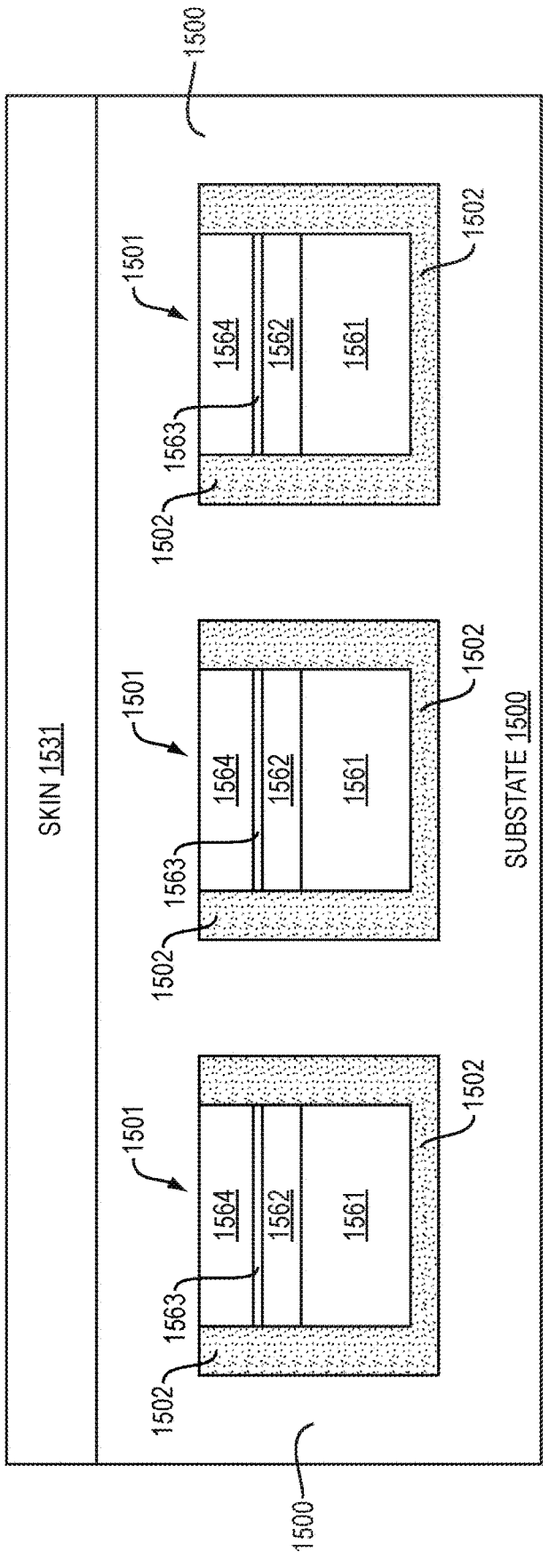
FIG. 15 shows phased arrays embedded in a substrate.

FIG. 15 shows phased arrays embedded in a substrate, in an illustrative implementation of this invention. FIG. 15 is a cross-sectional view. FIG. 15 shows a portion, but not all, of a substrate.

In FIG. 15, three phased arrays 1501 are each embedded in a substrate 1500. The phased arrays 1501 each comprise a backing layer 1561, an array 1562 of piezoelectric ultrasound transducers, electrodes 1563, and matching layer 1564.

In FIG. 15, each phased array is partially surrounded by an intermediate layer 1502. In FIG. 15, the intermediate layer 1502 for each given phased array surrounds the bottom and sides—but not the top—of the given phased array.

In FIG. 15, substrate 1500 conforms to and physically touches skin 1531.

For clarity of illustration, in FIG. 15, phased arrays 1501 are depicted as close to each other. In actual practice, however, ultrasound phased arrays may be much further apart from each other than is shown in FIG. 15. For instance, in some cases: (a) each phased array is about 2 centimeters distant from its nearest neighbor(s); and (b) the dimensions of each phased array is 6 mm×6 mm×1 mm.

For simplicity and clarity of illustration, FIG. 15 omits certain details. For instance, FIG. 15 does not show: (a) epoxy that is between individual transducers in a crystal array, and (b) data and power lines.

Image Reconstruction

In illustrative implementations of this invention: (a) each phased array in an ultrasound patch separately measures ultrasound reflections from a different volume of tissue; (b) the different volumes that are imaged by the different phased arrays partially overlap and are located at least partially in a target region of the tissue; and (c) based on the ultrasound measurements taken by the phased arrays, a 3D image of a volume of tissue is calculated.

In some cases, a conformable ultrasound transducer captures a 3D image of a region of tissue in a "single shot". Each "single shot" may consist of each piezoelectric ultrasound transducer in the patch pulsing once (and measuring reflection of the pulse). During a "single shot", different transducers in the patch may pulse at different times.

In some cases, the ultrasound transducers in the phased arrays perform electrical impedance and pulse-echo measurements, and are interfaced with a data acquisition system. In some cases, the data acquisition system includes a pulser/receiver, amplifier, high-voltage multiplexer, digital oscilloscope, impedance matching module, and interfacing software to transmit the pulse. The data acquisition system may control imaging parameters such as aperture size, transmit frequency, filtering, and time-gain compensation. The data acquisition system may operate multiple (e.g., 256) transmit/receive channels simultaneously, which may reduce the time length of data collection and the complexity of operation significantly. B-mode imaging may be performed to highlight soft tissues (e.g., from the breast) with the amplitude of the received signal from different inside reflectors and represented by gray scale values. Pulsed-echo signals may be generated from each phased array. An oscilloscope may acquire the signals with enough bandwidth and sampling frequency to receive the signals without distortion or aliasing.

In some cases, the reconstruction of 3-D images of a tissue includes three steps:

First Step: Each phased array in the patch may measure ultrasound reflections from tissue.

Second Step: A center ring array may be employed to determine the 3D position of each of the phased arrays. Accurate data regarding the relative positions of each phased array in a patch may be an input to the image processing algorithm. All of the phased arrays may be encapsulated in soft substrate (Ecoflex®). Thus, a sound wave may propagate along the soft substrate on the surface of soft tissue.

The intensity, frequency and speed of the propagation wave along the soft substrate surface may be measured.

Third Step: A 3-D image of an entire tissue region may be calculated, based on measurements taken by each of phased arrays. 3D positional data may be resampled to compute the 3D spatial coordinates (relative to the ring array) of each phased array. Even though the ultrasound patch may wrap around a curved body part (e.g., breast) conformably, precise 3-D images may be calculated for any angle and any given time point. According to the exact positional data of each 2-D array, the 3-D coverage from separate phased array images may be combined.

In some cases, image resolution is dependent upon working frequency and depth.

In some cases, a 3-D image of a large region of tissue is calculated based on a multitude of smaller 3-D images from phased arrays. The phased arrays may be located at different spatial positions relative to the tissue. Each phased array in the patch may take images (or measurements) independently from the other phased arrays in the patch.

In some cases, coverage gaps (between volumes sensed by the different phased arrays) may be minimized by (i) adding or reducing the number of phased arrays according to soft tissue volume, and (ii) combining individual images together according to their location on the soft tissue.

In some cases, an image from a single phased array may be generated by a reconstruction algorithm, including envelope detection and log compression wave mode structure adaptive weights, and matched coefficient approach. In some cases, the envelope data received is multiplied by the row elements when transmitting with columns, as well as the data received by the column elements when transmitting with rows, thereby achieving two-way focusing in both transmit and receive directions.

Machine Learning

In some implementations, a neural network (e.g., convolutional neural network) is trained on a large database of images that are generated by conformable ultrasound patches taking images of a curved body part of many different patients. Once trained, the neural network may be presented with a new, previously unseen image of tissue that has been captured by a conformable ultrasound patch. The trained neural network may, based on the new image, diagnose (or predict) a pathological condition in the tissue. For instance, the pathological condition may be a tumor.

In some cases, a pre-processing step applies different filters to reduce the effect of speckle, which the ultrasound images may contain. Local and global features, such as intensity, shadow, centrality, depth, may be calculated.

Prototype

The following nine paragraphs describe a prototype of this invention.

In this prototype, each ultrasound patch comprises multiple phased arrays. Interconnects between phased arrays and external power and data processing devices are aligned and bonded with heat seal connectors or other PI (polyimide)-based flexible cables. The phased arrays are bonded on Ecoflex® by UV ozone and hot-pressing at the designed position.

In this prototype, a phased array is encapsulated by silicon elastomer (Ecoflex®) in an ultrasound patch. The phased array comprises multiple transducers. Each transducer includes three parts: piezoelectric active element, backing layer, and matching layer.

In this prototype, a ring array consists of 24 elements, which are also made of same materials and structure as the phased array, with dimensions of 1 mm×1 mm×1 mm. The thickness of the patch is around 2.0 mm.

In this prototype, electric connections minimize signal noise and enhance electric performance. To fabricate a top electrode layer, Chromium (Cr)/Gold (Au) (10 nm/200 nm) is deposited on the upper surface by e-beam evaporation, and a polyimide (PI) layer is coated onto the electrode for encapsulation. A layer of photoresist is spin-coated on the electrode and patterned by mask aligner. Both the PI and Cr/Au electrode layers are dry etched by reactive ion etching and wet etched by a chemical etchant.

In this prototype, each ultrasound transducer comprises a single crystal of lead magnesium niobate-lead titanate, that is, $Pb(Mg_{1/3}Nb_{2/3})O_3$—$PbTiO_3$ (PMN-PT). This crystal exhibits high piezoelectric coefficients ($d_{33}$>2000 pC/N) and high electromechanical coupling factors ($k_{33}$=0.85 to 0.95). Pitch is equal to a half wavelength ($0.5\lambda$), which is satisfactory for both: (a) microfabrication and (b) avoiding side lobes ($<0.6\lambda$, to avoid side lobes). A row-column-addressed configuration of electrode connections: (a) reduces the number of interconnections by using a modified transmit/receive switching scheme; and (b) performs volumetric imaging of targets near the transducer using transmit beamforming in azimuth and receive beamforming in elevation.

In this prototype, a backing layer comprises a conductive epoxy mixture (E-SOLDER® 3022), which has good acoustic performance. During fabrication, the backing layer is centrifuged and lapped onto the single crystal uniformly. A transparent epoxy (EPO-TEK®301) is used to fill the kerf and eliminate the transverse vibration of the single crystals.

In this prototype, strain is reduced at the hard-component/soft-substrate interface. It is desirable to reduce the strain of this patch because the whole patch is rigid locally and soft globally. In this prototype, the interface between hard component (phased array) and soft substrate (Ecoflex®) is the highest mechanical loading point upon stretching of the device, due to the large difference in Young's modulus. The mechanical strain may be gradually distributed from the phased array to outside matching.

In this prototype, the top and bottom electrode connections are merged into one stretchable substrate, which would not only reduce the microfabrication complexity and avoids misalignment, but also improves the stretchability of the whole device.

In this prototype, an entire ultrasound patch is microfabricated in one batch, in a cleanroom facility. The microfabrication of the ultrasound patch involves sequential steps of spin-coating, baking, metallization, photolithography, etching, and transfer printing. The row-column addressing phased array is formed by two dice-and-fill steps using a (100)-poled PMN-PT single crystal with backing layer. This step ensures that the electrical connections of the row and column elements (64×64 elements) can be realized on the same surface of the piezoelectric layer. Subsequently, two dice-and-fill steps are carried along x- and y-axis directions with a pitch of 100 μm, and with Epoxy 301 (Epoxy Technology Inc.) being employed for filling/encapsulating.

The prototype described in the preceding nine paragraphs is a non-limiting example of this invention. This invention may be implemented in many other ways.

Computers

In illustrative implementations of this invention, one or more computers (e.g., servers, network hosts, client computers, integrated circuits, microcontrollers, controllers, microprocessors, field-programmable-gate arrays, personal computers, digital computers, driver circuits, or analog computers) are programmed or specially adapted to perform one or more of the following tasks: (1) to control the operation of, or interface with, hardware components of a ultrasound imaging system, including any ultrasound transducer and any phased array; (2) to control localization transducers; (3) to control transducers in a phased array to perform beam steering; (4) to calculate a 3D image of a volume of tissue, based on ultrasound measurements; (5) to receive data from, control, or interface with one or more patches; (6) to perform any other calculation, computation, program, algorithm, or computer function described or implied herein; (7) to receive signals indicative of human input; (8) to output signals for controlling transducers for outputting information in human perceivable format; (9) to process data, to perform computations, and to execute any algorithm or software; and (10) to control the read or write of data to and from memory devices (tasks 1-10 of this sentence being referred to herein as the "Computer Tasks"). The one or more computers (e.g., 1304, 1401, 1403, 1404, 1405) may, in some cases, communicate with each other or with other devices: (a) wirelessly, (b) by wired connection, (c) by fiber-optic link, or (d) by a combination of wired, wireless or fiber optic links.

In exemplary implementations, one or more computers are programmed to perform any and all calculations, computations, programs, algorithms, computer functions and computer tasks described or implied herein. For example, in some cases: (a) a machine-accessible medium has instructions encoded thereon that specify steps in a software program; and (b) the computer accesses the instructions encoded on the machine-accessible medium, in order to determine steps to execute in the program. In exemplary implementations, the machine-accessible medium may comprise a tangible non-transitory medium. In some cases, the machine-accessible medium comprises (a) a memory unit or (b) an auxiliary memory storage device. For example, in some cases, a control unit in a computer fetches the instructions from memory.

In illustrative implementations, one or more computers execute programs according to instructions encoded in one or more tangible, non-transitory, computer-readable media. For example, in some cases, these instructions comprise instructions for a computer to perform any calculation, computation, program, algorithm, or computer function described or implied herein. For instance, in some cases, instructions encoded in a tangible, non-transitory, computer-accessible medium comprise instructions for a computer to perform the Computer Tasks.

Network Communication

In illustrative implementations of this invention, electronic devices (e.g. 1304, 1401, 1403, 1404, 1405) are each configured for wireless or wired communication with other devices in a network.

For example, in some cases, one or more of these electronic devices each include a wireless module for wireless communication with other devices in a network. Each wireless module (e.g., 1305) may include (a) one or more antennas, (b) one or more wireless transceivers, transmitters or receivers, and (c) signal processing circuitry. Each wireless module may receive and transmit data in accordance with one or more wireless standards.

In some cases, one or more of the following hardware components are used for network communication: a computer bus, a computer port, network connection, network interface device, host adapter, wireless module, wireless card, signal processor, modem, router, cables and wiring.

In some cases, one or more computers (e.g. 1304, 1401, 1403, 1404, 1405) are programmed for communication over a network. For example, in some cases, one or more computers are programmed for network communication: (a) in accordance with the Internet Protocol Suite, or (b) in accordance with any other industry standard for communication, including any USB standard, ethernet standard (e.g., IEEE 802.3), token ring standard (e.g., IEEE 802.5), or wireless communication standard, including IEEE 802.11 (Wi-Fi®), IEEE 802.15 (Bluetooth®/Zigbee®), IEEE 802.16, IEEE 802.20, GSM (global system for mobile communications), UMT S (universal mobile telecommunication system), CDMA (code division multiple access, including IS-95, IS-2000, and WCDMA), LTE (long term evolution), or 5G (e.g., ITU IMT-2020).

DEFINITIONS

The terms "a" and "an", when modifying a noun, do not imply that only one of the noun exists. For example, a statement that "an apple is hanging from a branch": (i) does not imply that only one apple is hanging from the branch; (ii) is true if one apple is hanging from the branch; and (iii) is true if multiple apples are hanging from the branch.

To compute "based on" specified data means to perform a computation that takes the specified data as an input.

"Body part" means a part of a body of (a) a human or (b) an animal.

The term "comprise" (and grammatical variations thereof) shall be construed as if followed by "without limitation". If A comprises B, then A includes B and may include other things.

A non-limiting example of region A being "different than" region B occurs when region A partially overlaps region B.

A digital computer is a non-limiting example of a "computer". An analog computer is a non-limiting example of a "computer". A computer that performs both analog and digital computations is a non-limiting example of a "computer". However, a human is not a "computer", as that term is used herein.

"Computer Tasks" is defined above.

"Defined Term" means a term or phrase that is set forth in quotation marks in this Definitions section.

For an event to occur "during" a time period, it is not necessary that the event occur throughout the entire time period. For example, an event that occurs during only a portion of a given time period occurs "during" the given time period.

The term "e.g." means for example.

The fact that an "example" or multiple examples of something are given does not imply that they are the only instances of that thing. An example (or a group of examples) is merely a non-exhaustive and non-limiting illustration.

Unless the context clearly indicates otherwise, to say that X "extends" down Y describes a spatial extent of X and does not describe movement of X.

Unless the context clearly indicates otherwise: (1) a phrase that includes "a first" thing and "a second" thing does not imply an order of the two things (or that there are only two of the things); and (2) such a phrase is simply a way of identifying the two things, so that they each may be referred to later with specificity (e.g., by referring to "the first" thing and "the second" thing later). For example, if a device has a first socket and a second socket, then, unless the context clearly indicates otherwise, the device may have more than two sockets, and the first socket may occur in any spatial order relative to the second socket. A phrase that includes a "third" thing, a "fourth" thing and so on shall be construed in like manner.

"For instance" means for example.

To say a "given" X is simply a way of identifying the X, such that the X may be referred to later with specificity. To say a "given" X does not create any implication regarding X. For example, to say a "given" X does not create any implication that X is a gift, assumption, or known fact.

"Herein" means in this document, including text, specification, claims, abstract, and drawings.

A non-limiting example of an "image" is a visual image that is displayed by an electronic display screen. Another non-limiting example of an "image" is a set of data that encodes or represents a visual image.

As used herein: (1) "implementation" means an implementation of this invention; (2) "embodiment" means an embodiment of this invention; (3) "case" means an implementation of this invention; and (4) "use scenario" means a use scenario of this invention.

The term "include" (and grammatical variations thereof) shall be construed as if followed by "without limitation".

The "maximum dimension" of an object means the longest Euclidian distance between any two points on the exterior surface of the object.

Unless the context clearly indicates otherwise, "or" means and/or. For example, A or B is true if A is true, or B is true, or both A and B are true. Also, for example, a calculation of A or B means a calculation of A, or a calculation of B, or a calculation of A and B.

As used herein, a "phased array" or "ultrasound phased array" means a phased array that is configured to emit and to beam form ultrasound.

As used herein, the term "set" does not include a group with no elements.

Unless the context clearly indicates otherwise, "some" means one or more.

Skin "of" a body part means skin that is superficial to the body part.

As used herein, a "subset" of a set consists of less than all of the elements of the set.

"Substrate" means a layer or a sheet. A "substrate" may have objects embedded in it. A "substrate" may be curved or flat, and may bend or stretch as it changes shape. As used herein, the term "substrate" does not create any implication regarding the position of the substrate. For instance, the term "substrate" does not create any implication that the substrate is below any other object.

The term "such as" means for example.

As used herein, "time-of-flight" means an amount of time that elapses while an ultrasound pulse travels from a first location to a second location. "Times-of-flight" is the plural form of "time-of-flight".

As used herein, the terms "top", "bottom" and "side", in the context of surfaces of an object: (a) describe the position of the surfaces relative to each other; and (b) are not affected by the orientation of the object relative to a gravitational field. For instance: (a) the "top" and "bottom" surfaces of an object are opposite each other; (b) the "top" surface of an object continues to the "top" surface of the object, even if the object is tilted or flipped over; and (c) the "bottom" surface of an object continues to the "bottom" surface of the object, even if the object is tilted or flipped over. As used herein, the phrase "vertical height relative to" an object means vertical height in a local coordinate system of the object, in which local coordinate system "bottom" and "top" are construed in the manner set forth in the preceding sentence.

To say that a machine-readable medium is "transitory" means that the medium is a transitory signal, such as an electromagnetic wave.

"Ultrasound image" means an image calculated based on measurements of ultrasound.

Except to the extent that the context clearly requires otherwise, if steps in a method are described herein, then the method includes variations in which: (1) steps in the method occur in any order or sequence, including any order or sequence different than that described herein; (2) any step or steps in the method occur more than once; (3) any two steps occur the same number of times or a different number of times during the method; (4) one or more steps in the method are done in parallel or serially; (5) any step in the method is performed iteratively; (6) a given step in the method is applied to the same thing each time that the given step occurs or is applied to a different thing each time that the given step occurs; (7) one or more steps occur simultaneously; or (8) the method includes other steps, in addition to the steps described herein.

Headings are included herein merely to facilitate a reader's navigation of this document. A heading for a section does not affect the meaning or scope of that section.

This Definitions section shall, in all cases, control over and override any other definition of the Defined Terms. The Applicant or Applicants are acting as his, her, its or their own lexicographer with respect to the Defined Terms. For example, the definitions of Defined Terms set forth in this Definitions section override common usage and any external dictionary. If a given term is explicitly or implicitly defined in this document, then that definition shall be controlling, and shall override any definition of the given term arising from any source (e.g., a dictionary or common usage) that is external to this document. If this document provides clarification regarding the meaning of a particular term, then that clarification shall, to the extent applicable, override any definition of the given term arising from any source (e.g., a dictionary or common usage) that is external to this document. Unless the context clearly indicates otherwise, any definition or clarification herein of a term or phrase applies to any grammatical variation of the term or phrase, taking into account the difference in grammatical form. For example, the grammatical variations include noun, verb, participle, adjective, and possessive forms, and different declensions, and different tenses.

Variations

This invention may be implemented in many different ways. Here are some non-limiting examples:

In some implementations, this invention is a method comprising: (a) transmitting ultrasound signals and taking measurements of reflections of the signals, the transmitting and taking measurements being performed by a set of phased arrays embedded in a substrate, while the substrate touches skin of a body part; (b) detecting, based on measurements of other ultrasound signals, a set of three-dimensional (3D) positions of the phased arrays, each 3D position in the set of positions being a 3D position of a phased array in the set of arrays; and (c) calculating an image of tissue in the body part, based on the measurements of reflections and on the 3D positions of the phased arrays. In some cases, the image of tissue is a 3D image of a volume of the tissue. In some cases, the body part is a breast of a woman. In some cases, the body part is the shoulder or knee. In some cases, the body part is all or a portion of a finger, toe, wrist or ankle. In some cases, the detecting includes, for each specific phased array in the set of arrays, calculating location of the specific phased array, based on time elapsed while ultrasound travels to the specific phased array from each of at least three different ultrasound transducers in the substrate. In some cases: (a) the substrate includes a set of ultrasound transducers, other than the phased arrays; and (b) the detecting includes, for each specific phased array in the set of arrays (i) measuring times-of-flight of ultrasound that travels to the specific phased array from each of at least three ultrasound transducers in the substrate, which transducers are not part of the phased arrays, (ii) calculating, based on the times-of-flight, distances between the specific phased array and each of the at least three transducers, and (iii)

calculating, based on the distances, a location of the specific phased array relative to the three transducers. In some cases: (a) the substrate includes a set of ultrasound transducers, other than the phased arrays; and (b) the detecting includes, for each specific phased array in the set of arrays (i) measuring times-of-flight of ultrasound that travels to the specific phased array from each of at least three ultrasound transducers in the substrate, which transducers are not part of the phased arrays, (ii) calculating, based on the times-of-flight, distances between the specific phased array and each of the at least three transducers, (iii) calculating, based on the distances, an intersection of three spheres, and (iv) determining that the specific phased array is located at the intersection. In some cases: (a) the substrate includes a set of ultrasound transducers, other than the phased arrays; and (b) the detecting includes, for each specific phased array in the set of arrays (i) measuring a first time-of-flight of ultrasound that travels to the specific phased array from a first transducer in the set of transducers, (ii) measuring a second time-of-flight of ultrasound that travels to the specific phased array from a second transducer in the set of transducers, (iii) measuring a third time-of-flight of ultrasound that travels to the specific phased array from a third transducer in the set of transducers, (iv) calculating, based on the first time-of-flight, a first distance between the specific phased array and the first transducer, (v) calculating, based on the second time-of-flight, a second distance between the specific phased array and the second transducer, (vi) calculating, based on the third time-of-flight, a third distance between the specific phased array and the third transducer, and (vii) calculating that the specific phased array is located at an intersection of three spheres, which three spheres include a first sphere, second sphere and third sphere, the first sphere being centered on the first transducer and having a radius equal to the first distance, the second sphere being centered on the second transducer and having a radius equal to the second distance, and the third sphere being centered on the third transducer and having a radius equal to the third distance. In some cases, the transmitting involves the phased arrays each performing beam steering. In some cases, the taking measurements comprises measuring ultrasound that reflects from a set of regions in the tissue, in such a way that each phased array in the set of arrays measures ultrasound that reflects from a specific region in the set of regions, which specific region is different than that for each other phased array in the set of arrays. In some cases, each of the phased arrays is an array of piezoelectric ultrasound transducers. In some cases, the substrate adheres to the skin due to Van der Waals forces. Each of the cases described above in this paragraph is an example of the method described in the first sentence of this paragraph, and is also an example of an embodiment of this invention that may be combined with other embodiments of this invention.

In some implementations, this invention is an apparatus comprising: (a) an elastomeric substrate; (b) a set of phased arrays that are embedded in the substrate; (c) a set of transducers that are also embedded in the substrate; and (d) one or more computers; wherein (i) the phased arrays are configured to transmit ultrasound signals and take measurements of reflections of the signals, while the substrate touches skin of a body part, (ii) each specific phased array in the set of arrays is configured to measure times-of-flight of ultrasound signals that travel to the specific phased array from each of at least three transducers in the set of transducers, and (iii) the one or more computers are programmed (A) to calculate a set of three-dimensional (3D) positions of the set of phased arrays, in in such a way that, for each specific phased array in the set of arrays, 3D position of the specific phased array is computed based on the times-of-flight for the specific phased array, and (B) to calculate an image of a tissue in the body part, based on the measurements of reflections and on the set of 3D positions of the phased arrays. In some cases, the image of tissue is a 3D image of a volume of the tissue. In some cases, each of the phased arrays is an array of piezoelectric ultrasound transducers. In some cases, the substrate is configured to adhere to the skin due to Van der Waals forces. In some cases, each specific array, in the set of phased arrays: (a) includes piezoelectric ultrasound transducers; (b) also includes a conductive component, and (c) is electrically connected to a first set of wires and a second set of wires in such a way that (i) the first set of wires physically touches a first surface, which first surface is the top surface of the transducers in the specific array, (ii) the second set of wires physically touches a second surface, which second surface is the top surface of the conductive component, which conductive component extends from the second surface down a side of the specific array and under the specific array and physically touches the bottom side of the specific array, and (iii) the first and second surfaces are at equal vertical heights relative to the specific array. In some cases, for each given phased array in the set of arrays, a layer of material: (a) is located between, and physically touches, both the substrate and the given phased array; (b) partially surrounds the given phased array; and (c) has a Young's modulus that is greater than or equal to 60 kilopascals and less than or equal to 2 gigapascals. In some cases, the set of transducers are arranged in an annular spatial pattern. Each of the cases described above in this paragraph is an example of the apparatus described in the first sentence of this paragraph, and is also an example of an embodiment of this invention that may be combined with other embodiments of this invention.

Each description herein (or in the Provisional) of any method, apparatus or system of this invention describes a non-limiting example of this invention. This invention is not limited to those examples, and may be implemented in other ways.

Each description herein (or in the Provisional) of any prototype of this invention describes a non-limiting example of this invention. This invention is not limited to those examples, and may be implemented in other ways.

Each description herein (or in the Provisional) of any implementation, embodiment or case of this invention (or any use scenario for this invention) describes a non-limiting example of this invention. This invention is not limited to those examples, and may be implemented in other ways.

Each Figure, diagram, schematic or drawing herein (or in the Provisional) that illustrates any feature of this invention shows a non-limiting example of this invention. This invention is not limited to those examples, and may be implemented in other ways.

The above description (including without limitation any attached drawings and figures) describes illustrative implementations of the invention. However, the invention may be implemented in other ways. The methods and apparatus which are described herein are merely illustrative applications of the principles of the invention. Other arrangements, methods, modifications, and substitutions by one of ordinary skill in the art are also within the scope of the present invention. Numerous modifications may be made by those skilled in the art without departing from the scope of the invention. Also, this invention includes without limitation each combination and permutation of one or more of the items (including any hardware, hardware components, methods, processes, steps, software, algorithms, features, and technology) that are described herein.

The invention claimed is:

1. A method comprising:

transmitting ultrasound signals and taking measurements of reflections of the signals, the transmitting and taking measurements being performed by a set of phased arrays embedded in a substrate, while the substrate touches skin of a body part;

detecting, based on measurements of other ultrasound signals transmitted by a set of ultrasound transducers in the substrate arranged as an annular array and not part of the set of phased arrays, a set of three-dimensional (3D) positions of the set of phased arrays, each 3D position in the set of 3D positions being a 3D position of a phased array in the set of phased arrays; and calculating an image of tissue in the body part, based on the measurements of the reflections and on the 3D positions of the set of phased arrays.

2. The method of claim 1, wherein the image of the tissue is a 3D image of a volume of the tissue.

3. The method of claim 1, wherein the body part is a breast of a woman.

4. The method of claim 1, wherein the body part is shoulder or knee.

5. The method of claim 1, wherein the body part is all or a portion of a finger, toe, wrist or ankle.

6. The method of claim 1, wherein the detecting includes, for each specific phased array in the set of phased arrays, calculating location of the specific phased array, based on time elapsed while ultrasound travels to the specific phased array from each of at least three different ultrasound transducers of the set of ultrasound transducers.

7. The method of claim 1, wherein:

the detecting includes, for each specific phased array in the set of phased arrays measuring times-of-flight of ultrasound that travels to the specific phased array from each of at least three ultrasound transducers of the set of ultrasound transducers in the substrate, calculating, based on the times-of-flight, distances between the specific phased array and each of the at least three ultrasound transducers, and calculating, based on the distances, a location of the specific phased array relative to the at least three ultrasound transducers.

8. The method of claim 1, wherein:

the detecting includes, for each specific phased array in the set of phased arrays measuring times-of-flight of ultrasound that travels to the specific phased array from each of at least three ultrasound transducers of the set of ultrasound transducers in the substrate, calculating, based on the times-of-flight, distances between the specific phased array and each of the at least three ultrasound transducers, calculating, based on the distances, an intersection of three spheres, and determining that the specific phased array is located at the intersection.

9. The method of claim 1, wherein:

the detecting includes, for each specific phased array in the set of phased arrays measuring a first time-of-flight of ultrasound that travels to the specific phased array from a first transducer in the set of transducers, measuring a second time-of-flight of ultrasound that travels to the specific phased array from a second transducer in the set of transducers, measuring a third time-of-flight of ultrasound that travels to the specific phased array from a third transducer in the set of transducers, calculating, based on the first time-of-flight, a first distance between the specific phased array and the first transducer, calculating, based on the second time-of-flight, a second distance between the specific phased array and the second transducer, calculating, based on the third time-of-flight, a third distance between the specific phased array and the third transducer, and calculating that the specific phased array is located at an intersection of three spheres, which three spheres include a first sphere, second sphere and third sphere, the first sphere being centered on the first transducer and having a radius equal to the first distance, the second sphere being centered on the second transducer and having a radius equal to the second distance, and the third sphere being centered on the third transducer and having a radius equal to the third distance.

10. The method of claim 1, wherein the transmitting involves the set of phased arrays each performing beam steering.

11. The method of claim 1, wherein the taking measurements comprises measuring ultrasound that reflects from a set of regions in the tissue, in such a way that each phased array in the set of phased arrays measures ultrasound that reflects from a specific region in the set of regions, which specific region is different than that for each other phased array in the set of phased arrays.

12. The method of claim 1, wherein each of the set of phased arrays is an array of piezoelectric ultrasound transducers.

13. The method of claim 1, wherein the substrate adheres to the skin due to Van der Waals forces.

14. The method of claim 1, wherein the substrate is a substrate of a patch, wherein the annular array arrangement of the set of ultrasound transducers is located at a radial center of the patch.

15. The method of claim 14, wherein the set of phased arrays are located outside the radial center of the patch.

16. The method of claim 15, wherein the patch is segmented into a plurality of fan-shaped regions, each fan-shaped region including at least three ultrasound transducers of the set of ultrasound transducers and at least one phased array of the set of phased arrays.

17. The method of claim 16, wherein the fan-shaped regions allow localization of individual phased arrays of the set of phased arrays simultaneously with other phased arrays of the set of phased arrays being used to calculate the image of the tissue in the body part.

18. The method of claim 16, wherein at least one of the fan-shaped regions includes at least two phased arrays of the set of phased arrays.

* * * * *